US007606669B2

(12) United States Patent
Ohtsuka et al.

(10) Patent No.: US 7,606,669 B2
(45) Date of Patent: Oct. 20, 2009

(54) METHOD FOR PREDICTING CONCENTRATION DISTRIBUTION OF MICROPARTICLES, DEVICE FOR ANALYSIS, PROGRAM PRODUCT FOR PREDICTING CONCENTRATION DISTRIBUTION OF MICROPARTICLES, BUILDING AND DEVICE FOR DIFFUSING MICROPARTICLES DESIGNED BY USING THE METHOD FOR PREDICTION

(75) Inventors: Masaki Ohtsuka, Yao (JP); Yukishige Shiraichi, Yao (JP)

(73) Assignee: Sharp Kabushiki Kaisha, Osaka (JP)

( * ) Notice: Subject to any disclaimer, the term of this patent is extended or adjusted under 35 U.S.C. 154(b) by 243 days.

(21) Appl. No.: 11/597,055

(22) PCT Filed: Apr. 22, 2005

(86) PCT No.: PCT/JP2005/007680

§ 371 (c)(1), (2), (4) Date: Nov. 20, 2006

(87) PCT Pub. No.: WO2005/114058

PCT Pub. Date: Dec. 1, 2005

(65) Prior Publication Data

US 2008/0133147 A1 Jun. 5, 2008

(30) Foreign Application Priority Data

May 21, 2004 (JP) ............................ 2004-152225

(51) Int. Cl.
*G01N 31/00* (2006.01)
*G06F 19/00* (2006.01)

(52) U.S. Cl. ........................... 702/24; 702/19; 702/119; 702/177

(58) Field of Classification Search .................. 702/24, 702/119, 177, 19; 382/110; 703/11; 204/157.3, 204/157.15; 422/177, 186; 73/61.42
See application file for complete search history.

(56) References Cited

FOREIGN PATENT DOCUMENTS

| | | | |
|---|---|---|---|
| JP | 2004-28518 | A | 2/2004 |
| JP | 2004-61068 | A | 2/2004 |
| JP | 2004-101058 | A | 4/2004 |
| JP | 2005-55089 | A | 3/2005 |

OTHER PUBLICATIONS

Shuzo Murakami, "New scales for ventilation efficiency and their application based on numerical simulation of room airflow", Internal Symposium on Room Air Convection Ventilation Effectiveness, University of Tokyo, Jul. 22-24, 1992, p. 22-38.*

Stewart et al., "Prediction of indoor gaseous pollutant dispersion by nesting sub-zones within a multizone model", Building and Environment 38 (2003), pp. 635-643.*

Faulkner et al., "Indoor Air Flow and Pollutant Removal in a Room with Desk-Top Ventilation", Apr. 1993.*

Kazuhide Ito et al., CFD Analysis and Model Experiment of Ozone Distribution in 2D Test Room, J. Environ. Eng. AIJ, Mar. 2004, pp. 33-40, No. 577.

* cited by examiner

*Primary Examiner*—John H Le
(74) *Attorney, Agent, or Firm*—Birch, Stewart, Kolasch & Birch, LLP

(57) ABSTRACT

A method for predicting local concentrations of short-lived microparticles having an unstable composition in a room simply and in a short time is provided. The method for predicting the concentration distribution of microparticles includes the steps of determining a flow field in a room, determining the age-of-air distribution in the room on the basis of the flow field in the room, and converting the age of air into the concentration of the microparticles.

22 Claims, 24 Drawing Sheets

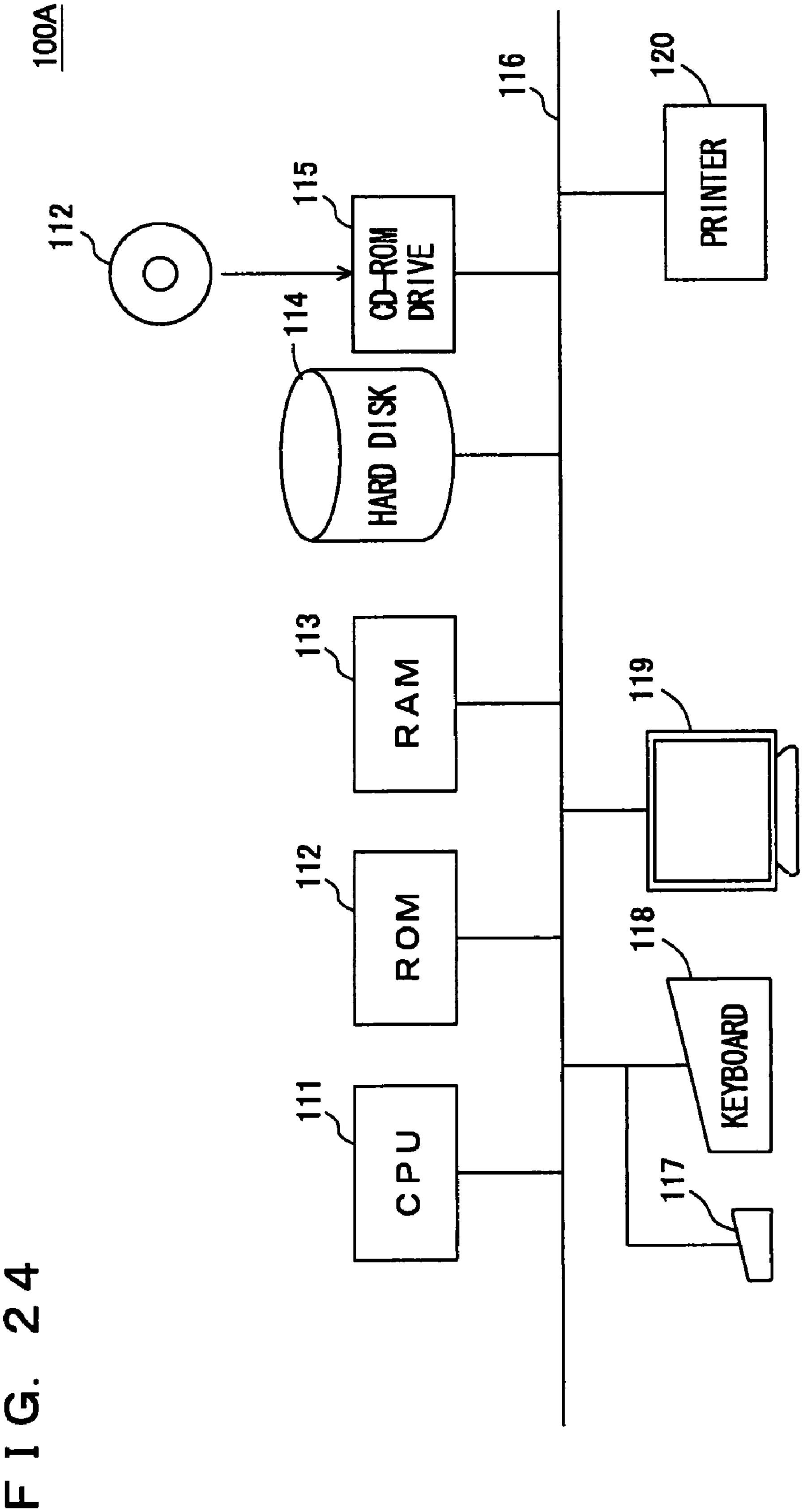
F I G. 2 4

METHOD FOR PREDICTING CONCENTRATION DISTRIBUTION OF MICROPARTICLES, DEVICE FOR ANALYSIS, PROGRAM PRODUCT FOR PREDICTING CONCENTRATION DISTRIBUTION OF MICROPARTICLES, BUILDING AND DEVICE FOR DIFFUSING MICROPARTICLES DESIGNED BY USING THE METHOD FOR PREDICTION

TECHNICAL FIELD

The present invention relates to a method for predicting the concentration distribution of microparticles, an analyzer, a program for predicting the concentration distribution of microparticles, and a building and a microparticle diffusing device designed by the prediction method. More particularly, the present invention relates to a method for predicting the concentration distribution of microparticles in which local concentrations of the microparticles discharged into a room space are determined by a numerical analysis, an analyzer, a program product for predicting the concentration distribution of microparticles, and a building and a microparticle diffusing device designed by the prediction method.

BACKGROUND ART

In recent years, products having an air cleaning effect, disinfection effects, or relaxation effects (for example, an air conditioner or an air cleaner) have been increasing. These products achieve the effects by diffusing ions or mist (tiny drops of water), mist containing a fragrant component or a medicinal component, or microparticles such as water vapor in a room. In designing these products, there is a need for a method for determining local concentrations of microparticles discharged into a room space by a numerical analysis. For example, Japanese Patent Laying-Open No. 2004-028518 (Patent Document 1) discloses a method for designing a clean room that can appropriately reduce fine particles by monitoring the number distribution of fine particles in the clean room.

A flow field analysis system that analyzes a flow field in a room to determine local directions, local velocities, and local temperatures of air currents has been commercialized. A known indoor flow field analysis system includes the steps of constructing an analytical model in which a room is divided into microelements to analyze a flow field in the room, inputting a boundary condition to simulate the flow field with the analytical model, analyzing the analytical model with the boundary condition to determine the flow field defined by the directions, the velocities, and the temperatures of air currents at the microelements.

A known flow field analysis system employs a mass conservation formula, a momentum conservation formula, a turbulent energy conservation formula, and a turbulent dissipation conservation formula to determine the flow field. In addition to these conservation formulae, an energy conservation formula is employed to determine the temperature distribution.

This known analysis system in combination with a diffusion equation of a material allows the determination of indoor local concentrations of microparticle contaminants having a stable composition (for example, $CO_2$, $NO_2$, or water vapor) in the air and the analysis of diffusive behavior of the microparticles in the room. However, many equations must be solved. This makes the computation complicated and causes many computational errors. Thus, the concentration distribution could not be determined accurately. Furthermore, since these equations are defined theoretically, the theoretical diffusive behavior of particles may be different from the actual diffusive behavior of the particles under a certain condition.

Another method analyzes a flow field in a room to determine local ages of air in the room and thereby determine the age-of-air distribution in a living room. This method further includes a step of determining the age-of-air distribution in the room on the basis of the conventional analysis of the flow field in the room. For example, Japanese Patent Laying-Open No. 2004-101058 (Patent Document 2) discloses an analysis system for designing a ventilation system having an improved ventilation efficiency. This system explicitly defines the effects of a plurality of air outlets and air inlets on the age of air and the life expectancy of air at a point of measurement in a room.

Patent Document 1: Japanese Patent Laying-Open No. 2004-028518

Patent Document 2: Japanese Patent Laying-Open No. 2004-101058

DISCLOSURE OF THE INVENTION

Problems to be Solved by the Invention

The present invention was achieved to solve the problems described above. One object of the present invention is to provide a method for predicting the concentration distribution of microparticles, an analyzer, a program product for predicting the concentration distribution of microparticles, a building and a microparticle diffusing device designed by the prediction method. The prediction method can simply and quickly predict local concentrations of short-lived microparticles having an unstable composition in a room.

Means for Solving the Problems

To achieve the aforementioned object, a method for predicting the concentration distribution of microparticles according to one aspect of the present invention includes the steps of determining a flow field in a room, determining the age-of-air distribution in the room on the basis of the flow field in the room, and converting the age of air into the concentration of the microparticles.

The term "age of air" refers to the time required for air to move from a starting point to another point. The age of air at a starting point is taken as zero. For example, the time required for air to move from a starting point to another point may be expressed as a mean value, a maximum value, or a minimum value.

According to the present invention, the concentration of microparticles can easily be determined at any location in a room by converting the age of air determined from the flow field in the room into the concentration of the microparticles. The concentration of short-lived microparticles having a relatively unstable composition can simply and quickly be determined at any location in a room.

Preferably, in the converting step, the age of air is converted into the concentration of microparticles using a predetermined relation depending on the type of microparticles.

According to the present invention, the concentration of microparticles can be determined in a manner that depends on the type of microparticles.

Preferably, the predetermined relation defines the relationship between the elapsed time t and the concentration X of microparticles.

Preferably, the relation is expressed by the following equation (1) defined by constants α, β, γ, and δ. The constant β depends on the starting point of elapsed time.

$$X(t)=\alpha/(t-\beta)+\gamma, X(t)\geqq\delta \quad (1)$$

According to the present invention, the constants α, β, γ, and δ in the equation (1) depend on the type of microparticles. The concentration at the starting point of elapsed time can be changed by changing the constant β. The term "starting point of elapsed time" refers to the time when the age of air is zero. The starting point of elapsed time defines the location of fine particles at an age of air of zero. For example, the location of fine particles at an age of air of zero may be the location of microparticles immediately after their generation or the location of microparticles at which the microparticles are discharged into a room. Thus, the concentration of microparticles can be predicted for microparticles of different types and microparticles of different concentrations at the starting point.

Preferably, in the converting step, the age of air is converted into the concentration of microparticles using a predetermined relation depending on the number of generated microparticles.

Preferably, the relation defines the relationship between the elapsed time t and the attenuation rate of microparticles.

Preferably, the relation is expressed by the following equation (2) defined by constants $\alpha_1$ and $\beta_1$. The constant $\beta_1$ depends on the number of generated microparticles.

$$dX/dt=-\alpha_1 X^2, X(0)=1/\beta_1 \quad (2)$$

According to the present invention, the constants $\alpha_1$ and $\beta_1$ in the equation (2) depend on the type of microparticles. The concentration of microparticles at the starting point can be changed by changing the constant $\beta_1$. Thus, the concentration distribution of microparticles in a room can be predicted for microparticle of different types and microparticles of different concentrations at the starting point.

Preferably, the prediction method according to the present invention further includes the steps of constructing an analytical model in which a room is divided into microelements and setting a boundary condition to simulate the flow field. The step of determining a flow field in a room further includes the substeps of determining a flow field in a room on the basis of the boundary condition and parameters defining the analytical model and changing the boundary condition to determine a boundary condition corresponding to a concentration of microparticles that satisfies a predetermined condition among the concentration of microparticles.

According to the present invention, an optimum boundary condition can be determined.

Preferably, the boundary condition includes the direction and the velocity of an air current.

Preferably, the prediction method according to the present invention further includes the steps of constructing an analytical model in which a room is divided into microelements, setting a boundary condition to simulate the flow field, and changing the parameters defining the analytical model to determine parameters corresponding to a concentration of microparticles that satisfies a predetermined condition among the concentration of microparticles.

According to the present invention, parameters defining an optimum analytical model can be determined.

Preferably, the parameters include the size of a room, the shape of the room, and the installation location of a microparticle generator.

Preferably, the prediction method according to the present invention further includes the step of changing the concentration of microparticles at the starting point of elapsed time to determine the concentration of microparticles at a starting point corresponding to a concentration of microparticles that satisfies a predetermined condition among the concentration of microparticles.

According to the present invention, the optimum concentration of microparticles at the starting point can be determined.

Preferably, the parameters include the size of a room, the shape of the room, and the concentration of microparticles at the starting point.

Preferably, microparticles may be composed of at least one selected from the group consisting of ions, tiny drops of water, and tiny drops of water containing a fragrant component.

Preferably, a program product for predicting the concentration distribution of microparticles that causes a computer to execute the method for predicting the concentration distribution of microparticles is provided.

Preferably, a building includes a room defined by parameters defining an analytical model in which a room is divided into microelements, when the concentration distribution of microparticles determined by the method for predicting the concentration distribution of microparticles satisfies a predetermined condition.

Preferably, the microparticle diffusing device has a boundary condition for simulating the flow field and the concentration at a starting point, when the concentration distribution of microparticles determined by the method for predicting the concentration distribution of microparticles satisfies a predetermined condition.

BRIEF DESCRIPTION OF THE DRAWINGS

FIG. 24 is a schematic block diagram illustrating a hardware configuration of a computer.

DESCRIPTION OF THE REFERENCE SIGNS

1 indoor unit, 4 air inlet, 5 air outlet, 10 microparticle diffusing device, 11 circulator, 12 air cleaner, 20, 21 room, 100 analyzer, 101 control unit, 102 analytical model construction unit, 103 flow field analysis unit, 104 age-of-air analysis unit, 105 conversion unit, 106 output unit, 100A computer, 114 hard disk, 115 CD-ROM drive, 116 bus, 117 mouse, 118 keyboard, 119 display, 120 printer.

BEST MODES FOR CARRYING OUT THE INVENTION

Embodiments of the present invention will be described below with reference to the drawings. In the following description, the same components are denoted by the same reference signs. Their designations and functions are also the same. Therefore, their detailed explanation will not be repeated.

First Embodiment

Figure 1:
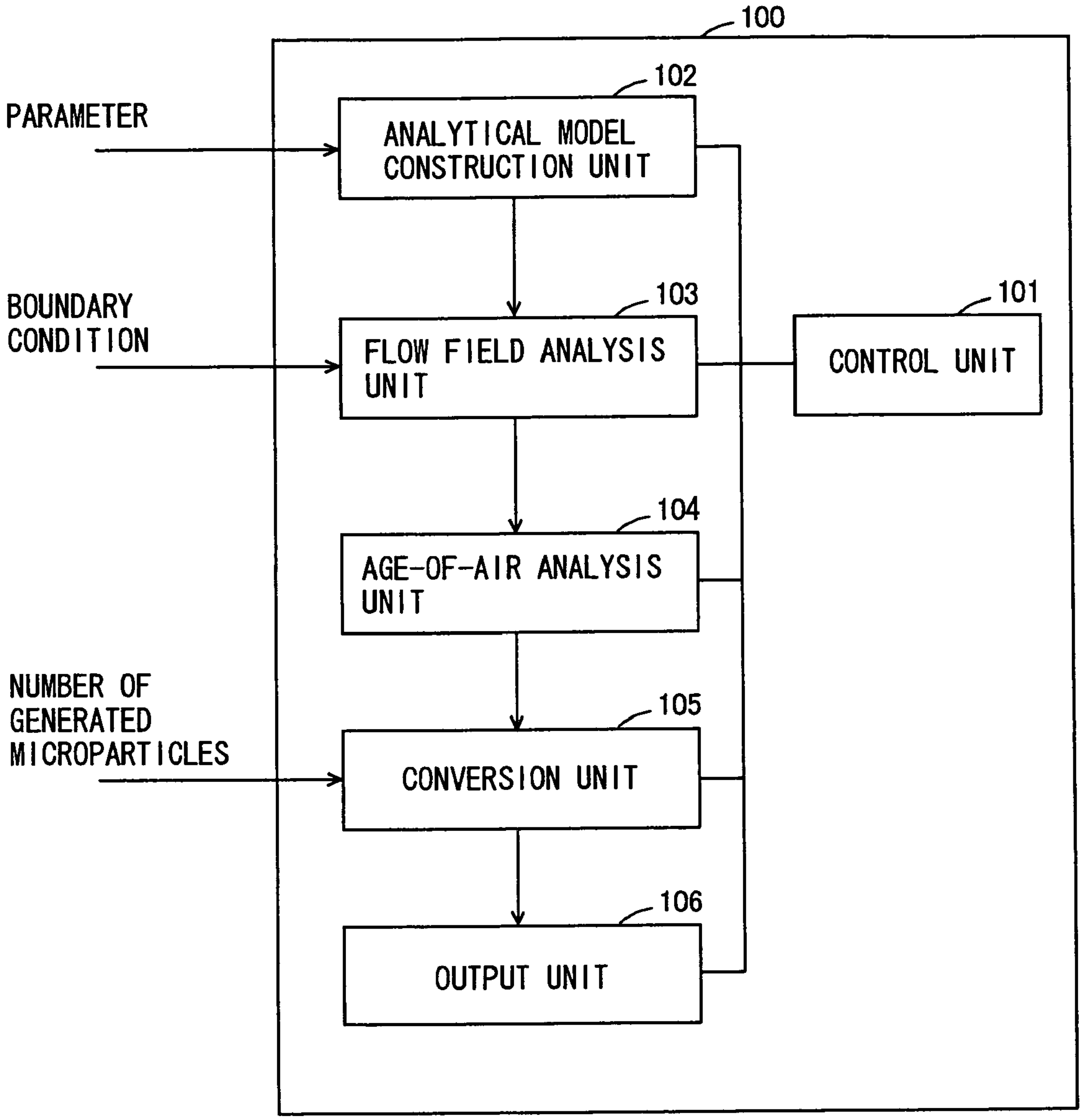
FIG. 1 is a schematic block diagram illustrating the function of an analyzer according to a first embodiment of the present invention.

FIG. 1 is a schematic block diagram illustrating the function of an analyzer according to a first embodiment of the present invention. With reference to FIG. 1, analyzer 100 includes control unit 101 for controlling the entire analyzer, analytical model construction unit 102 for constructing an analytical model with which the flow field in a room is analyzed, flow field analysis unit 103 for applying a boundary condition to the analytical model to analyze the flow field, age-of-air analysis unit 104 for determining the age-of-air distribution in the room from the flow field, conversion unit 105 for converting the age of air into the concentration of microparticles, and output unit 106 for outputting the concentration of microparticles.

In analytical model construction unit 102, a room is divided into microelements to construct an analytical model with which the flow field in the room is analyzed. Parameters for defining an analytical model are input to analytical model construction unit 102. The parameters include the shape and the size (length, width, and height) of a room and the arrangement (the concentration of microparticles at a starting point) and the number of microparticle diffusing devices. An analytical model constructed in analytical model construction unit 102 is output to flow field analysis unit 103. A microparticle diffusing device includes a microparticle generator and a fan for generating an air current. The microparticle diffusing device discharges microparticles generated by the microparticle generator into a room on air currents generated by the fan. Furthermore, the microparticle generator can control the voltage applied to the microparticle generator and thereby control the number of microparticles to be generated.

Flow field analysis unit 103 receives the input of a boundary condition for simulating the flow field. The boundary condition includes the velocity, the volume, and the temperature of an air current sent from an air outlet (suction port), and the temperature of a room. Flow field analysis unit 103 calculates the direction and the pressure of an air current at each microelement of the analytical model constructed by analytical model construction unit 102 under the boundary condition. The direction and the pressure of an air current at each microelement define the flow field. The direction and the pressure of an air current at each microelement are output to age-of-air analysis unit 104.

Age-of-air analysis unit 104 calculates the age of air at each microelement on the basis of the direction and the pressure of an air current at corresponding microelement calculated in flow field analysis unit 103. The age of air at each microelement is output to conversion unit 105.

The term "age of air" refers to the time required for air to move from a starting point to a point of interest. The age of air at a starting point is taken as zero. The starting point defines the reference of the age of air. For example, the time required for air to move from a starting point to a point of interest (elapsed time from the starting point) may be expressed as a mean value, a maximum value, or a minimum value of the time required for air to move from a starting point to a point of interest. The term "starting point" refers to a location at which the age of air is zero. For example, the location of fine particles at an age of air of zero may be the location of microparticles immediately after their generation or the location at which the fine particles are discharged into a room.

Conversion unit 105 calculates the concentration of microparticles at each microelement by substituting the age of air into a predetermined numerical formula that defines the relationship between the elapsed time from a starting point and the concentration of microparticles. The concentration of microparticles calculated at each microelement is output to output unit 106.

Output unit 106 is a display, such as a liquid crystal display, a plasma display panel, or a cathode-ray tube, or a printing device, such as a printer. Output unit 106 outputs the concentration of microparticles at each microelement.

Then, the method for converting the age of air into the concentration of microparticles by conversion unit 105 will be described below. In this embodiment, it is postulated that diffused microparticles have an unstable composition and are short-lived. In this case, the life of microparticles must be taken into consideration. The concentration of microparticles X(t) at an elapsed time t from a starting point is expressed by the relation (1):

$$X(t)=\alpha/(t-\beta)+\gamma,\ X(t)\geqq\delta \qquad (1)$$

wherein α, β, γ, and δ are constants. The constants α, β, γ, and δ depend on the type of ions or diffused microparticles. In particular, the constant β depends on the starting point of age of air. These constants can be determined in an experiment in which the concentration is measured by generating microparticles. Any number of microparticles can be generated in the experiment. The starting point is taken as the time point when microparticles are generated. The constant β is determined on the basis of the number of generated microparticles. The constant β for the number of generated microparticles that is different from the number of generated microparticles used in the experiment can be calculated backwards from the concentration X(0) of microparticles at t=0 in the relation (1), which is set to the target number of generated microparticles. Thus, when the constants α, β, γ, and δ are determined in the experiment, the relation (1) applicable to any number of generated microparticles can be obtained by changing the constant β.

When a mixture of almost equal numbers of positive ions $H^+(H_2O)_n$ (n is an integer not less than 0) and negative ions $O_2^-(H_2O)_m$ (m is an integer not less than 0) were diffused in a room, the constants were found to have the following values by measurement. Thus, these values are used herein as the constants.

α=50000/11

β=0

γ=−2700

δ=1000

The values (X=X1, X=X2, X=X3, . . . , X=Xn) calculated by substituting the local age of air (t=t1, t=t2, t=t3, . . . , t=tn) determined by a step of determining the age-of-air distribution in a room into the relation (1) are taken as local concentrations of microparticles in the room. Thus, local concentrations of microparticles can be calculated from corresponding local age of air.

Figure 2:
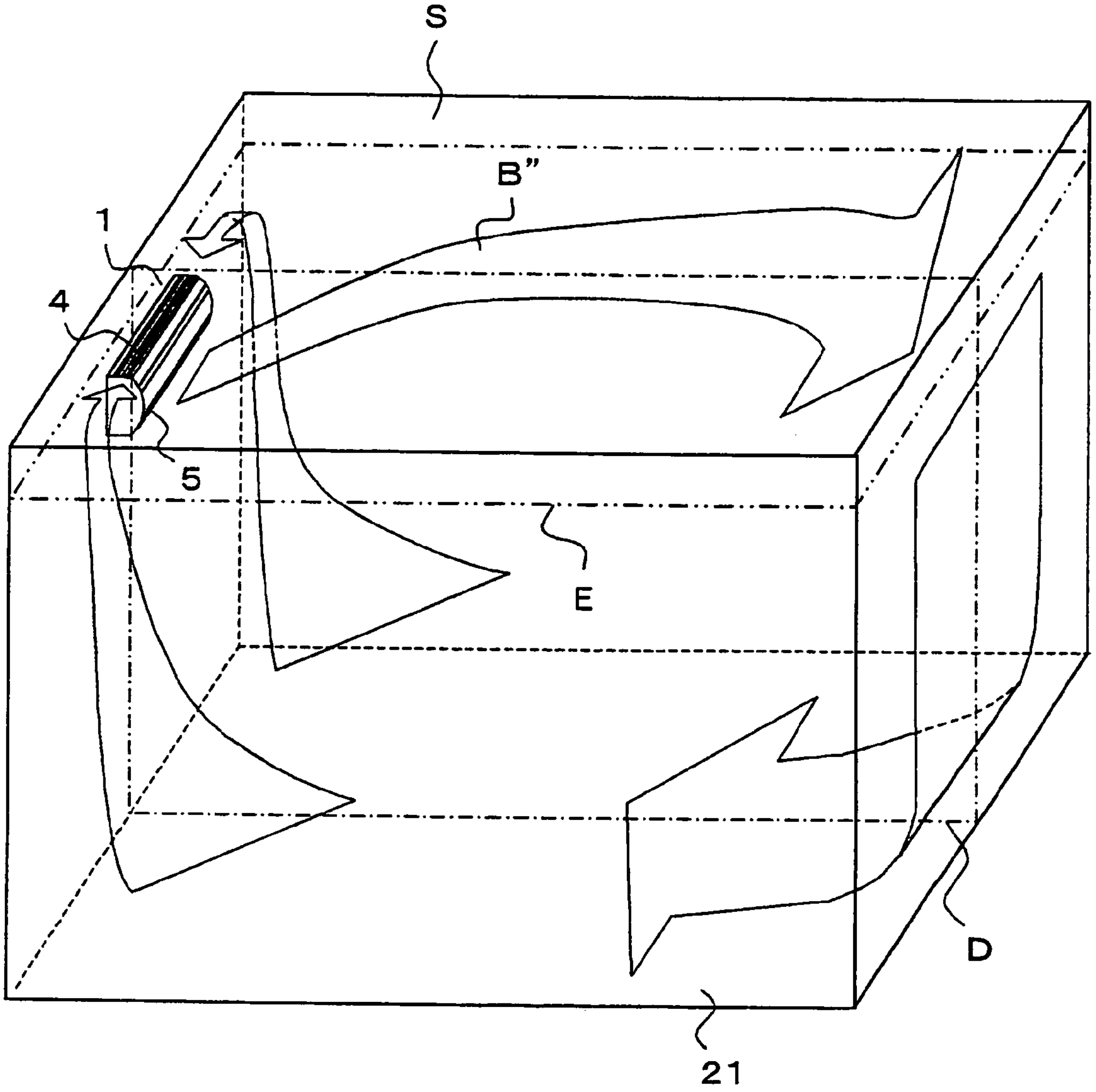
FIG. 2 is a schematic view illustrating an analytical sample.

The ion concentration distribution predicted by the analyzer 100 and the ion concentration observed when ions are diffused in a room from an actual product are compared as described below. FIG. 2 is a schematic view illustrating an analytical sample. In the analytical sample, an indoor unit 1 of an air conditioner diffuses a mixture of almost equal numbers of positive ions $H^+(H_2O)_n$ and negative ions $O_2^-(H_2O)_m$ in room 21.

FIG. 2 illustrates the behavior of air currents in the room from the sample air conditioner. Air (B") sent obliquely upward at a velocity of 4 m/s from air outlet 5 of indoor unit 1 of the air conditioner reaches the ceiling S of room 21. Then, because of the Coanda effect, the air flows along the ceiling S, a wall opposite to indoor unit 1 of the air conditioner, the floor, and a wall on which indoor unit 1 is placed, and is drawn from both sides of indoor unit 1 into air inlet 4 of indoor unit 1. Room 21 is 8 mats in size (2400 mm in height, 3600 mm in width, and 3600 mm in depth). Comparison is performed at a central cross section of room 21 indicated by an alternate long and short dashed line D and a horizontal cross section 200 mm below the ceiling S indicated by a chain double-dashed line E in FIG. 2.

Figure 3A:
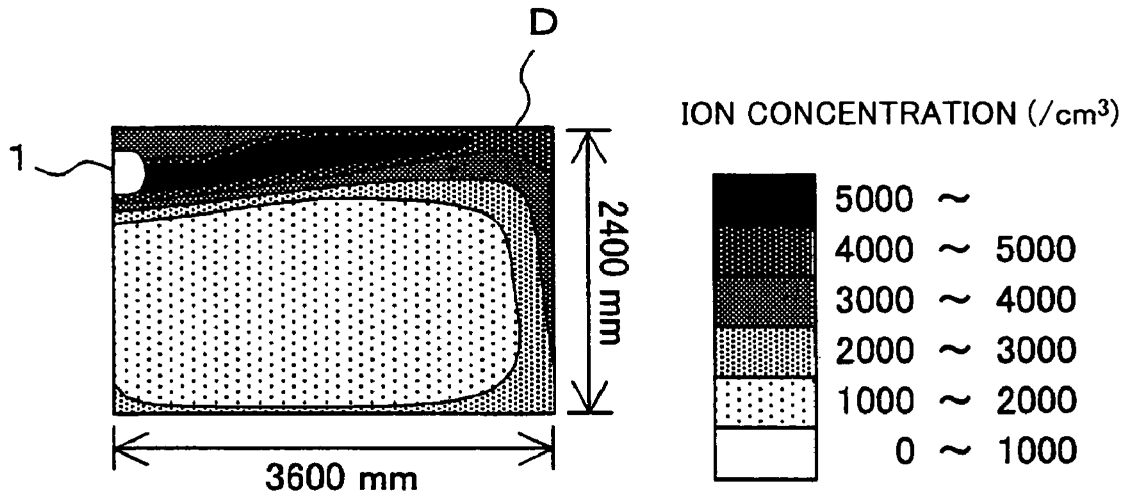
FIG. 3A is a graph illustrating a result predicted by an analyzer.
Figure 3B:
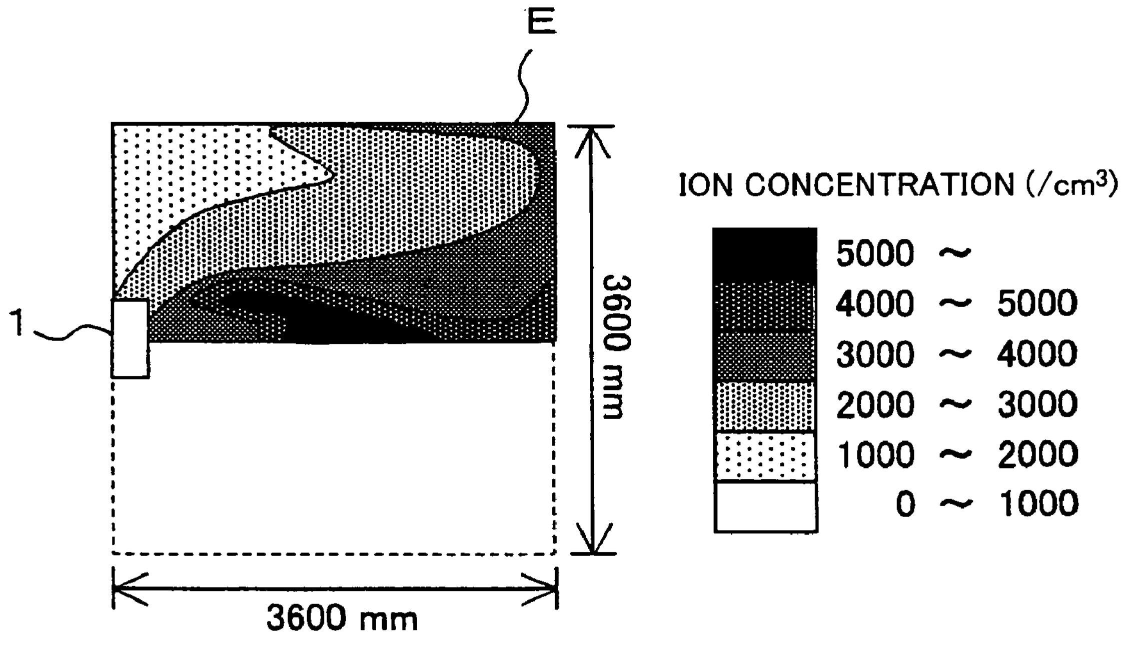
FIG. 3B is a graph illustrating another result predicted by an analyzer.

FIGS. 3A and 3B illustrate results predicted by the analyzer. FIG. 3A illustrates a predictive ion concentration distribution at the central cross section D of room 21. FIG. 3B illustrates a predictive ion concentration distribution at the horizontal cross section E of room 21. A mixture of almost equal numbers of positive ions $H^+(H_2O)_n$ and negative ions $O_2^-(H_2O)_m$ is diffused in the room.

FIG. 3B illustrates the upper half of the ion concentration distribution at the horizontal cross section E, because the upper half and the lower half are symmetrical in the analytical model. The ion concentration distribution may be illustrated on the entire horizontal cross section E. For example, the concentrations of the two ion species in the vicinity of the position at which the ions are generated are one million/$cm^3$ each.

Figure 4A:
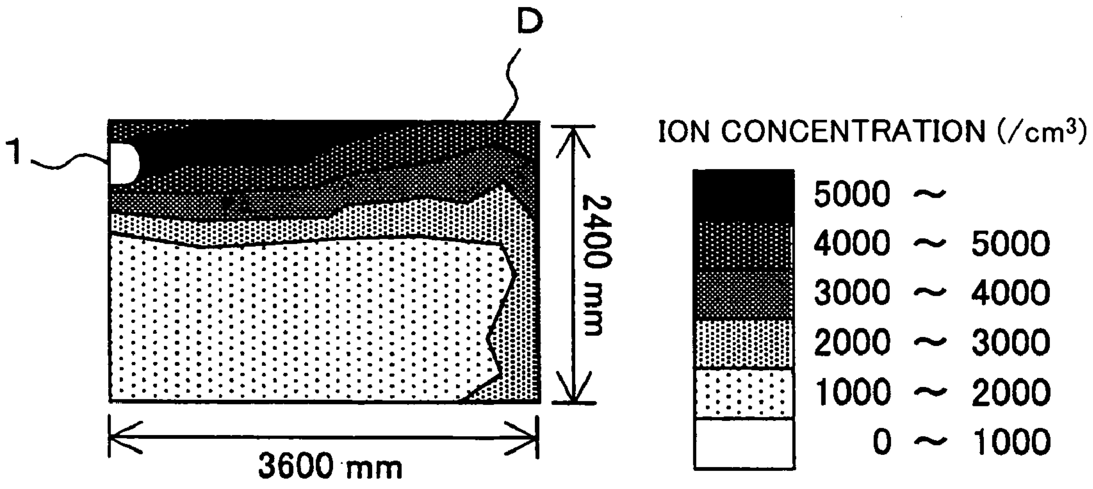
FIG. 4A is a graph illustrating an observed result.
Figure 4B:
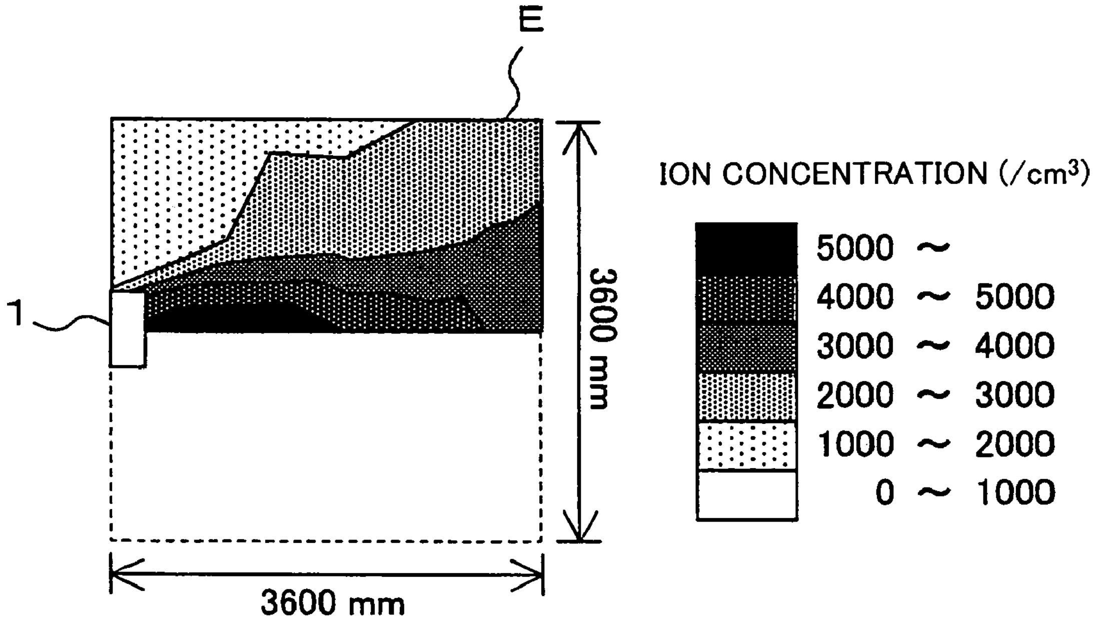
FIG. 4B is a graph illustrating another observed result.

FIGS. 4A and 4B illustrate observed results. FIG. 4A illustrates an observed ion concentration distribution at the central cross section D of room 21. FIG. 4B illustrates an observed ion concentration distribution at the horizontal cross section E of room 21. FIGS. 4A and 4B illustrate the observed results of ion concentration distribution, when a mixture of almost equal numbers of positive ions $H^+(H_2O)_n$ and negative ions $O_2^-(H_2O)_m$ are diffused in the room. FIG. 4B illustrates the upper half of the ion concentration distribution at the horizontal cross section E. Because the upper half and the lower half are symmetrical in the analytical model, the experimental value of the ion concentration distribution is also assumed to be almost symmetrical. Thus, no measurement is performed in the lower half. Furthermore, to match the state of ion generation to the predictive analysis, an ion generator is controlled so that the concentrations of the two ion species are one million/$cm^3$ each in the vicinity of the ion generator.

FIGS. 3A, 3B, 4A, and 4B show that the predictive values are in very good agreement with the observed values. These results indicate the usefulness of analyzer 100 according to the present embodiment or the validity of a technique for converting the age of air into the concentration of microparticles.

Furthermore, a relation representing the relationship between the elapsed time t from the discharge of microparticles and the concentration X of microparticles may be used instead of the relation (1). In this case, the constant β of the relation (1) is determined by the concentration at a starting point where microparticles are discharged.

Figure 5:
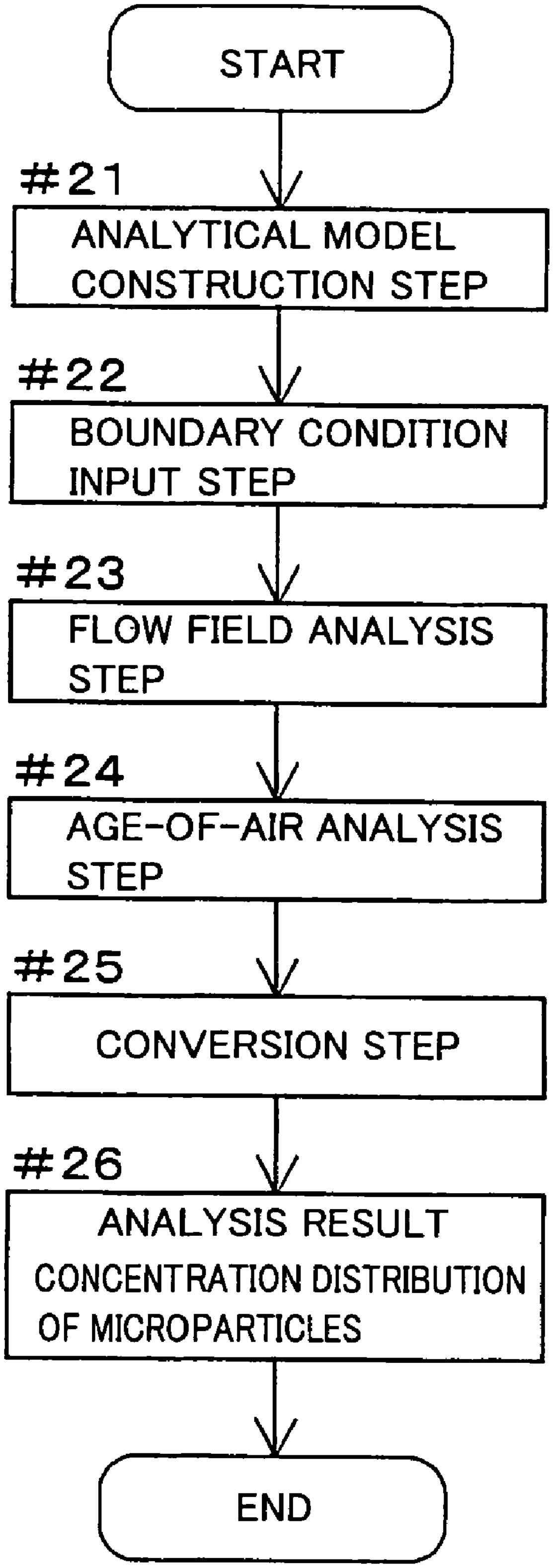
FIG. 5 is a flow chart of processes executed by an analyzer according to a first embodiment.

FIG. 5 is a flow chart of processes executed by an analyzer according to a first embodiment. When analyzer 100 starts an analysis, analyzer 100 constructs an analytical model in which a room is divided into microelements to analyze a flow field in a room in step #21 of constructing an analytical model. In this step, the shape of the room, the location of an air current outlet (suction port), the location of an air current inlet (exhaust port), the arrangement of furniture, and the like are modeled. Then, for convenience' sake, the space is divided into lattices of microelements for computation.

Then, in step #22 of inputting a boundary condition, a boundary condition for simulating the flow field with the analytical model constructed in step #21 is input to analyzer 100 by a user of analyzer 100. The boundary condition includes the velocity, the volume, and the temperature of an air current sent from an air outlet (suction port), and the temperature of the room. Then, in step #23 of analyzing the flow field, analyzer 100 analyzes the analytical model with the boundary condition to determine the flow field defined by the direction, the velocity, and the temperature of the air current at each lattice of the microelements.

In the next step #24, analyzer 100 determines the ages of air on the basis of the results of the flow field analysis obtained in step #23. Then, in step #25, analyzer 100 converts the results of the age-of-air analysis obtained in step #24, that is, the ages of air into the concentrations of microparticles. Thus, the concentrations of microparticles are calculated. Then, in step #26, analyzer 100 displays the analysis results. It is desirable to visually display the analysis results by making a distribution chart from the concentrations of microparticles.

As described above, for example, analyzer 100 can easily design a building that exhibits very large effects of microparticle diffusion without complicated processes such as an experiment and can greatly reduce the design cost. Furthermore, for example, in placing or installing microparticle diffusing devices in a room, one can previously know a suitable arrangement and the number of devices. Thus, the installation can easily be performed with very large effects of microparticle diffusion and without complicated processes such as an experiment. This can reduce the time required to place or install the microparticle diffusing devices and greatly reduce the cost. In addition, for example, in a step of designing a microparticle diffusing device, the directions and the volumes of air currents and the number of generated microparticles can easily be set to optimize the diffusion of microparticles in a room in which the device is to be installed. Thus, a microparticle diffusing device that can maximize the effects of microparticle diffusion can easily be designed without complicated processes such as an experiment.

Second Embodiment

Next, an analyzer according to a second embodiment will be described below. The analyzer according to the second embodiment is different from the analyzer according to the first embodiment in a technique for converting the age of air into the concentration of microparticles. Otherwise, the analyzer according to the second embodiment is identical with the analyzer according to the first embodiment. Thus, the same description will not be repeated. A conversion technique used by the analyzer according to the second embodiment includes a relation representing the relationship between the elapsed time t from a starting point and the attenuation rate of microparticles.

In this embodiment, a mixture of almost equal numbers of positive ions $H^+(H_2O)_n$ and negative ions $O_2^-(H_2O)_m$ is diffused in the room. These two types of ions collide with each other and are known to react with each other according to the following equations (3) to (5).

Specifically, the positive ions $H^+(H_2O)_n$ and the negative ions $O_2^-(H_2O)_m$ collide and react with each other into other substances. Thus, the number of collisions per unit volume and unit time represents the attenuation of the number or the concentration of ions. Since the numbers of $H^+(H_2O)_n$ and $O_2^-(H_2O)_m$ in a unit volume are almost the same, the number of collisions Z per unit volume and unit time is expressed by the following equation (6). In this equation, n denotes the number of ions in a unit volume. C denotes the average velocity. σ denotes the collision radius.

Furthermore, a relation expressed by an equation (7) holds between the concentration $X_H$ of $H^+(H_2O)_n$ and the concentration $X_O$ of $O_2^-(H_2O)_m$. Thus, the attenuation rate of ions is expressed by a relation (8), wherein $\alpha_1$ is a constant.

Solving this differential equation leads to a relation (9), wherein $\alpha_1$ and $\beta_1$ are constants.

Using the relation (9), local concentrations of microparticles are calculated from corresponding local ages of air in a room by the same process as in the analyzer according to the first embodiment. The constants $\alpha_1$ and $\beta_1$ depend on the type and the generation state of ions or diffused microparticles. These constant terms must therefore be determined by a proper technique such as an experiment. The constant $\beta_1$ is the reciprocal of the concentration of microparticles at a starting point.

[Numerical Formula 1]

$$H^+(H_2O)_n + O_2^-(H_2O)_m \rightarrow OH + 1/2\,O_2 + (n+m)H_2O \quad (3)$$

$$H^+(H_2O)_n + H^+(H_2O)_n + O_2^-(H_2O)_m + O_2^-(H_2O)_m \rightarrow 2\cdot OH + O_2 + (n+n'+m+m')H_2O \quad (4)$$

$$H^+(H_2O)_n + H^+(H_2O)_n + O_2^-(H_2O)_m + O_2^-(H_2O)_m \rightarrow H_2O_2\cdot + O_2(n+n'+m+m')H_2O \quad (5)$$

$$Z = Z = \frac{\pi(2\sigma)^2\cdot 2^{1/2}}{2}\cdot c\cdot n^2 \quad (6)$$

$$X \approx X_H \approx X_O \quad (7)$$
$$n \propto X$$

-continued $$dX/dt = -\alpha_1 X^2 \quad (8)$$

$$X(t) = \frac{1}{\alpha_1 t + \beta_1},\ X(0) = \frac{1}{\beta_1},\ \beta_1 > 0 \quad (9)$$

Analyzer 100 according to the second embodiment can provide predictive analysis results almost identical with those of analyzer 100 according to the first embodiment. Furthermore, a relation representing the relationship between the elapsed time t from the diffusion of microparticles and the concentration X of microparticles may be used instead of the relation (2). In this case, the constant $\beta_1$ of the relation (2) is determined by the concentration at a starting point where microparticles are discharged.

Third Embodiment

Examples of a method for diffusing microparticles in a room include a method in which a microparticle diffusing device is installed in a room and a method in which microparticles are diffused on air currents from a microparticle outlet placed on a wall in a room. Examples of a microparticle diffusing device installed in a room include an air conditioner, a humidifier, an air cleaner, and other various devices. When microparticles are diffused from a microparticle outlet placed on a wall in a room, various locations of the outlet, various blow directions, and various velocities of air currents may be contemplated. The location of a microparticle diffusing device in a room, the location of a microparticle outlet, the blow direction, and the velocity of an air current affect the diffusibility of microparticles, such as negative ions, water vapor, tiny drops of water, or a fragrant component, in a room. In particular, when diffused microparticles have limited lives, the diffusibility of microparticles in a room is extremely affected. The installation location of a microparticle diffusing device or a microparticle outlet or the blow direction and the blowing velocity of microparticles relative to the size and the shape of a room in which the device is installed must be taken into account to optimize the diffusibility of microparticles in the room.

An analyzer according to a third embodiment constructs an analytical model on the basis of given parameters, determines the flow field of the analytical model with a given boundary condition and a given concentration at a starting point, and determines the age of air at each microelement of the analytical model. The age of air is converted into the concentration of microparticles by the relation (1). Thus, the analyzer determines the concentration of microparticles at each microelement of the analytical model from the given parameters, the given boundary condition, and the given concentration at a starting point. Then, the analyzer determines the parameters, the boundary condition, and the concentration at a starting point to provide the optimum concentration of microparticles in the room. Thus, the analyzer determines the size of the room, the shape of the room, the installation location of a microparticle diffusing device or a microparticle outlet, and the blow direction and the blowing velocity of microparticles to optimize the diffusibility of microparticles in the room.

The analyzer according to the third embodiment differs from the analyzer according to the first embodiment or the second embodiment in that various design parameters and a boundary condition optimum or suitable for the diffusion of microparticles in a room are determined. Other factors are the same as the analyzer according to the first embodiment or the second embodiment and therefore, their explanation will not be repeated here.

Figure 6:
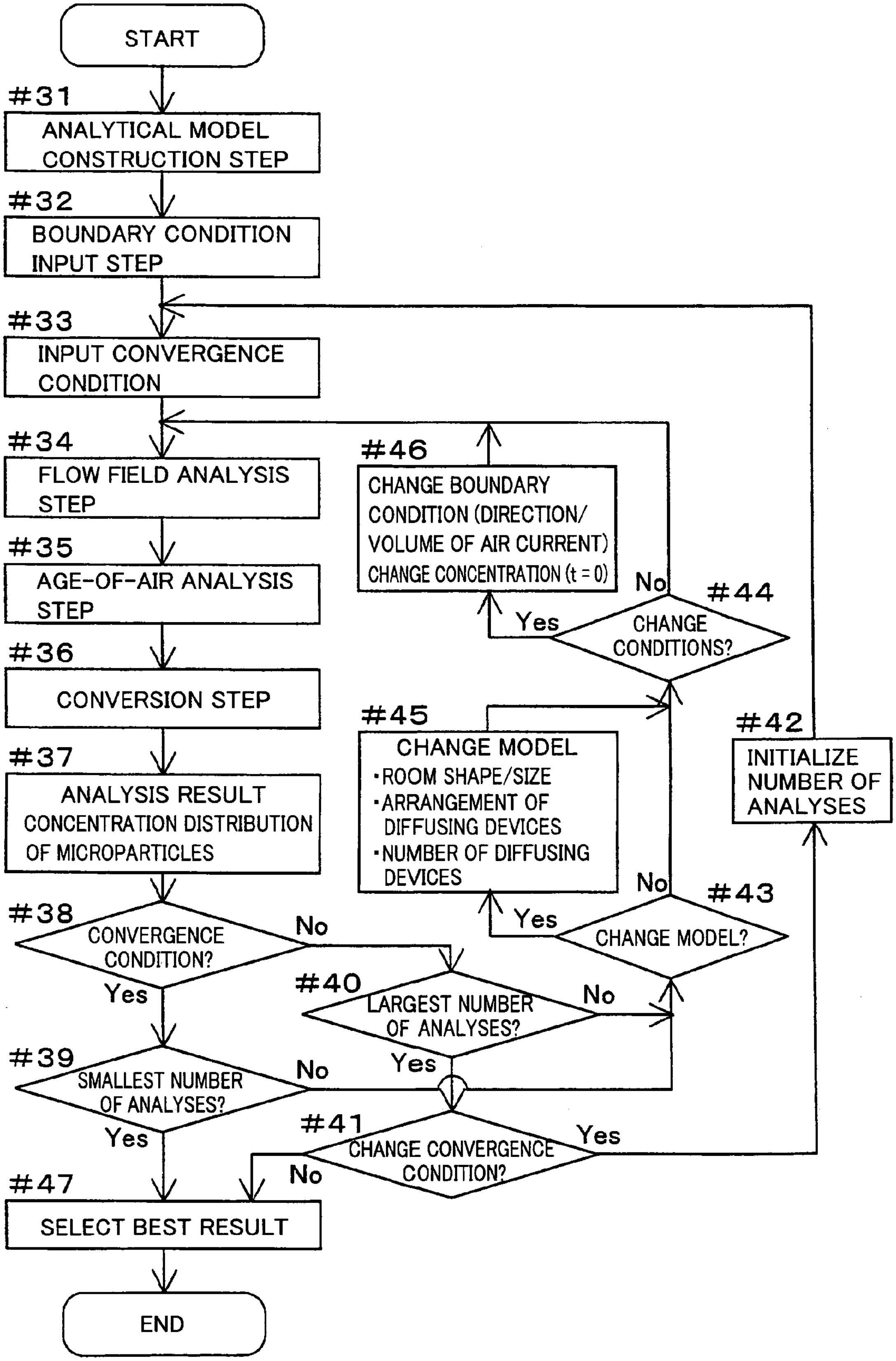
FIG. 6 is a flow chart of processes executed by an analyzer according to a third embodiment.

FIG. 6 is a flow chart of processes executed by the analyzer according to the third embodiment. Specifically, processes of steps #31 and #32 are the same as the processes of steps #21 and #22 executed by analyzer 100 according to the first embodiment in FIG. 5. Thus, the explanation of these processes will not be repeated. In step #33, the analyzer receives the input of convergence condition.

Microparticles often have different effects depending on their types. The effects often vary in strength with the concentration of the microparticles. An appropriate concentration of microparticles must be diffused in a room to optimize the diffusibility of microparticles in the room. In this step, a desired concentration condition under which the effects of microparticles can be exploited is set over the entire room or in part of the room. For example, the concentration of microparticles in the entire room is at least $10000/cm^3$, the concentration of microparticles in the upper half of the room is at least $3000/cm^3$ and that in the lower half of the room is at least $5000/cm^3$, or the concentration of microparticles at the center of the room is at least $50000/cm^3$ and that in the rest is at least $5000/cm^3$.

A user of the analyzer specifies the largest number of analyses and the smallest number of analyses. Depending on the convergence condition, one analysis is sufficient to satisfy the convergence condition. In this case, the result may not be optimum. It is therefore desirable that the smallest number of analyses is previously specified and the analyzer selects the best result among the results of the smallest number of analyses. Depending on the convergence condition, any number of analyses may be insufficient to satisfy the convergence condition. To avoid wasting the processing time, it is desirable that the largest number of analyses is previously specified and, when the largest number of analyses is insufficient to satisfy the convergence condition, the analyzer selects the best result among the results of the largest number of analyses. Furthermore, the convergence condition desirably includes a condition concerning the velocity of an air current; for example, the velocity of 0.2 m/s or less in a predetermined space at the center of a room.

The processes of steps #34 to #37 are the same as the processes of steps #23 to #26 executed by the analyzer according to the first embodiment. In step #38, the analyzer compares local concentrations of microparticles in a room determined in step #37 with the convergence condition specified in step #31 and judges whether the local concentrations of microparticles in a room satisfy the convergence condition or not. When the local concentrations of microparticles in a room satisfy the convergence condition (YES in step #38), the process proceeds to step #39. When the local concentrations of microparticles in a room do not satisfy the convergence condition (NO in step #38), the process proceeds to step #40.

In step #39, to increase the precision of optimization, the analyzer judges whether the number of analyses at this point reaches the smallest number of analyses specified in step #33 or not. When the number of analyses reaches the smallest number of analyses (YES in step #39), the process proceeds to step #47. When the number of analyses does not reach the smallest number of analyses (NO in step #39), the process proceeds to step #43. In step #40, to avoid wasting the processing time, the analyzer judges whether the number of analyses at this point reaches the largest number of analyses specified in step #33 or not. When the number of analyses reaches the largest number of analyses (YES in step #40), the process proceeds to step #41. When the number of analyses does not reach the largest number of analyses (NO in step #40), the process proceeds to step #43.

In step #41, a process is performed if the convergence condition is not still satisfied when the number of analyses reaches the largest number of analyses. In this case, because the convergence condition may be improper, whether the convergence condition is to be changed or not is judged. When the convergence condition is not changed (NO in step #41), the process proceeds to step #47. When the convergence condition is changed (YES in step #41), the process proceeds to step #42 to initialize the number of analyses and then proceeds to step #33.

The process proceeds to step #43 and step #44 when the analysis result does not satisfy the convergence condition. The analytical model or the boundary condition or both are partly changed. In step #43, whether the analytical model is to be changed or not is judged. When the analytical model is not changed (NO in step #43), the process proceeds to step #44. When the analytical model is changed (YES in step #43), the process proceeds to step #45.

In addition, in step #44, whether the boundary condition is to be changed or not is judged. When the boundary condition is not changed (NO in step #44), the process proceeds to step #34. When the boundary condition is changed (YES in step #44), the process proceeds to step #46. In steps #43 and #44, at least one of the analytical model and the boundary condition must be changed.

In step #45, parameters defining the analytical model are changed. The parameters include the shape and the size of a room and the arrangement (the concentration of microparticles at a starting point) and the number of microparticle diffusing devices. As a method for changing the analytical model, a golden section method, a David-Fletcher-Powel (DFP) method, or another appropriate method is applied to a parameter to be changed. The analytical model can be replaced by a more appropriate analytical model on the basis of the results.

In step #46, the boundary condition or the number of generated microparticles is changed. The boundary condition includes the direction and the volume of an air current from the microparticle diffusing device. As a method for changing the boundary condition or the number of generated microparticles, a golden section method, a DFP method, or another appropriate method is applied to a parameter to be changed. On the basis of the results, a user of the analyzer can use a more appropriate boundary condition or the more appropriate number of generated microparticles.

In step #47, the best result is selected from a plurality of analysis results thus obtained. The shape and the size of a room, the arrangement and the number of microparticle diffusing devices, the volume and the direction of an air current, and the number of generated microparticles in the best result are returned as optimal solutions. The analysis is thus completed.

For example, the analyzer according to the third embodiment can easily design a building that exhibits very large effects of microparticle diffusion without complicated processes such as an experiment and can greatly reduce the design cost. For example, when a constructor places or installs microparticle diffusing devices in a room, the constructor can previously know a suitable arrangement and the suitable number of devices. Thus, the constructor can easily perform the installation having very large effects of microparticle diffusion without complicated processes such as an experiment. This can reduce the time required to place or install the microparticle diffusing devices and greatly reduce the cost. In addition, for example, in a step of designing a microparticle diffusing device, a user of the analyzer can easily set the directions and the volumes of air currents and the number of generated microparticles to optimize the diffusion of microparticles in a room in which the device is to be installed. Thus, the user can easily obtain a microparticle diffusing device that can maximize the effects of microparticle diffusion without complicated processes such as an experiment.

Fourth Embodiment

Figure 7:
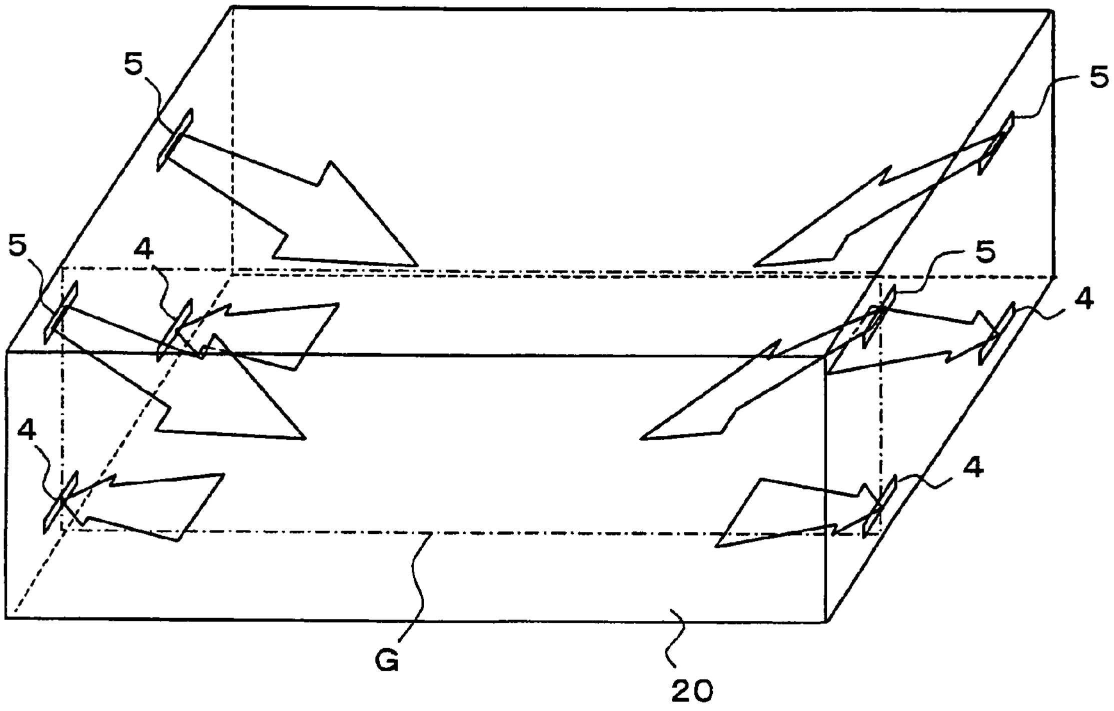
FIG. 7 is another schematic view illustrating the behavior of air currents in a room.

Rooms designed with the analyzers according to the first to third embodiments will be described below. FIG. 7 is another schematic view illustrating the behavior of air currents in a room. In FIG. 7, room 20 is 32 mats in size (2400 mm in height, 7200 mm in width, and 7200 mm in depth). Two air outlets 5 for discharging microparticles into the room are separately placed on the upper part of one side wall of room 20. The microparticles are mixed with air currents sent from microparticle diffusing device 10. Air inlets 4 for exhausting air from the room are placed substantially beneath two air outlets 5. In the same manner, two air outlets 5 and two air inlets 4 are placed on the opposite side wall. Arrows illustrated in FIG. 7 indicate the behavior of air currents sent from air outlets 5 in the room at an angle of 30 degrees downward from the horizontal at a velocity of 4 m/s. The air sent from air outlets 5 immediately loses momentum, is drawn from air inlets 4, and is discharged outside the room.

Figure 8:
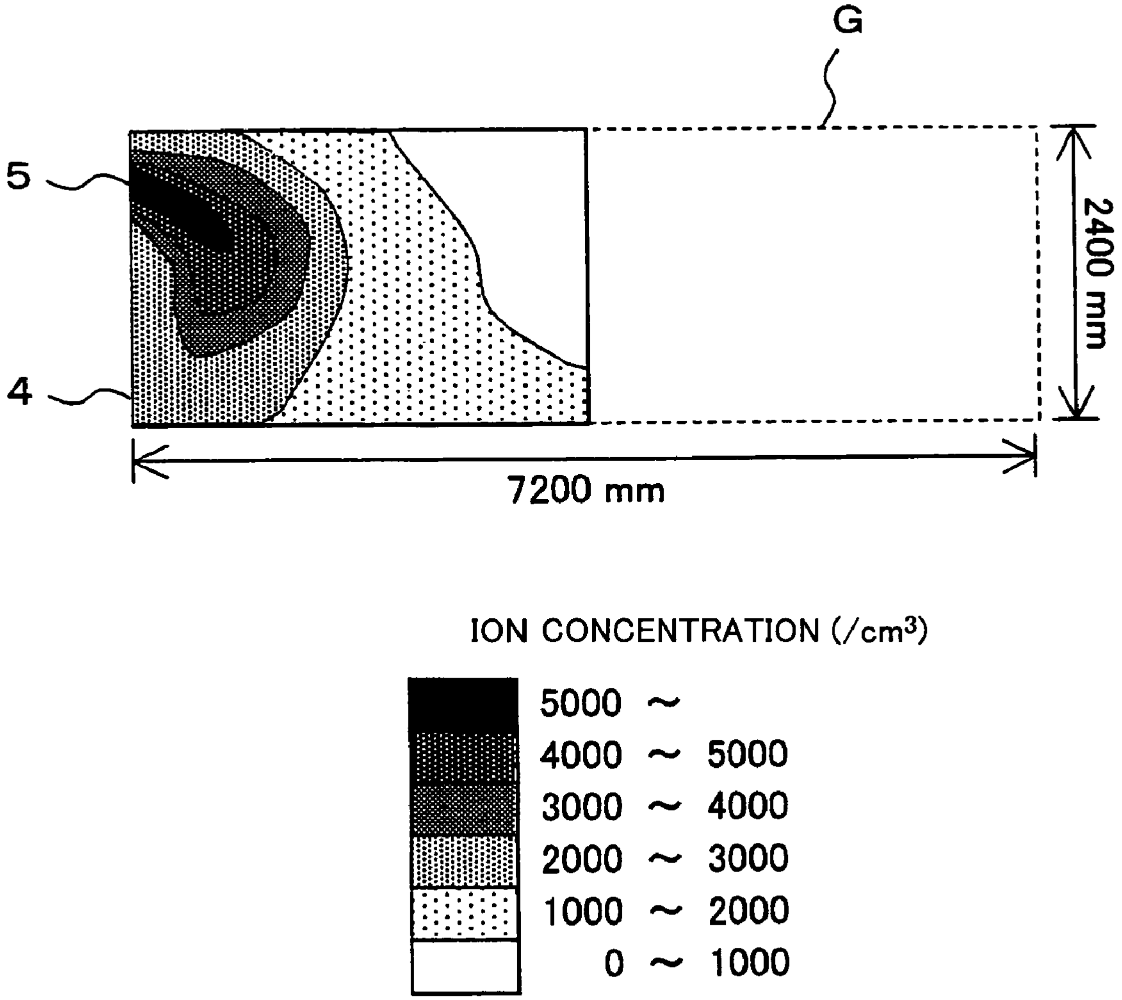
FIG. 8 is a graph illustrating another predicted result of the concentration distribution of microparticles.

FIG. 8 is a graph of another predicted result of the concentration distribution of microparticles. FIG. 8 illustrates only the left half of a predictive ion concentration distribution at a cross section G passing through the center of air outlets 5 and air inlets 4 illustrated in FIG. 7. Because the right half and the left half are symmetrical with respect to a line, FIG. 7 illustrates only the left half of the cross section G and omits the right half. FIG. 8 illustrates the concentration distribution of ions in room 20 predicted by the system according to the first embodiment, when a mixture of equal numbers of positive ions $H^+(H_2O)_n$ and negative ions $O_2^-(H_2O)_m$ is sent from air outlets 5 as microparticles. In this embodiment, for example, the concentrations of the two ion species in the vicinity of the position at which the ions are generated are also one million/$cm^3$ each.

FIG. 8 shows that a region having an ion concentration of less than 2000/$cm^3$ spreads over the center of the room. Furthermore, a region having an ion concentration of less than 1000/$cm^3$ exists at the upper center of the room. Hence, the ions do not spread over the entire room. Academic research has already showed that at least 99% of airborne viruses die in two hours in a space containing at least 2000/$cm^3$ of $H^+(H_2O)_n$ and $O_2^-(H_2O)_m$ each. Hence, in room 20 illustrated in FIGS. 7 and 8, the effect of killing airborne viruses is insufficient.

Figure 9:
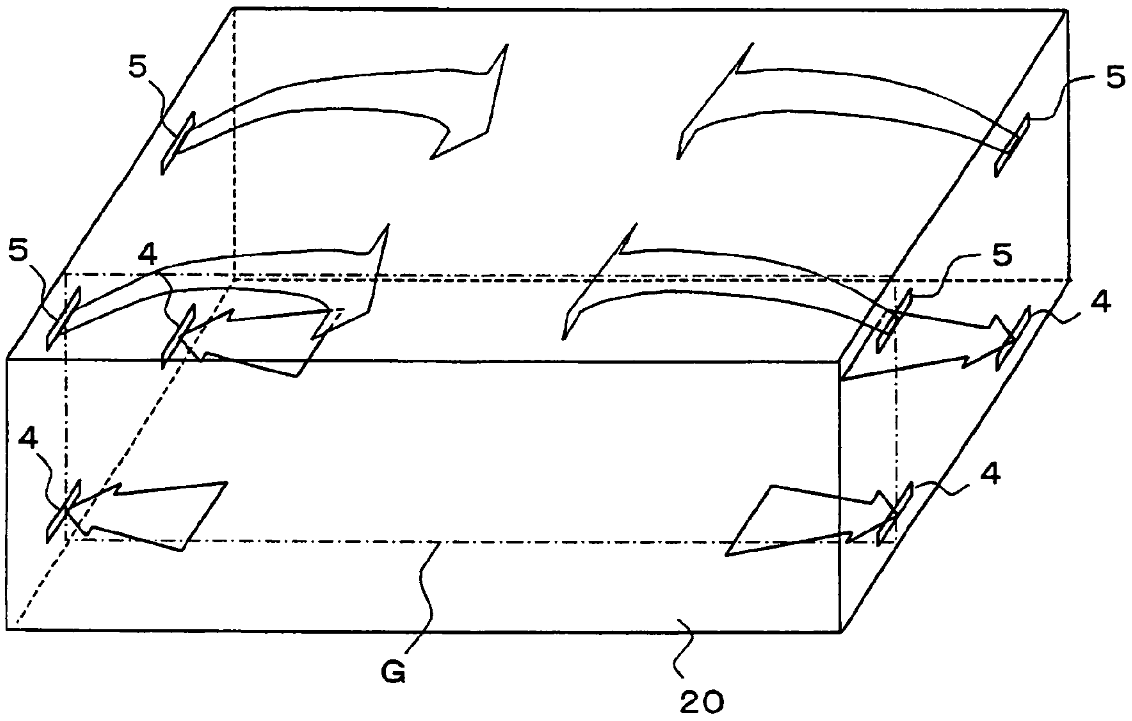
FIG. 9 is still another schematic view illustrating the behavior of air currents in a room.

Then, another model is intended to send air currents from air outlets 5 at an angle of 20 degrees upward from the horizontal at a velocity of 4 m/s. FIG. 9 is still another schematic view illustrating the behavior of air currents in the room. FIG. 9 illustrates the behavior of air currents sent from air outlets 5 in the room at an angle of 20 degrees upward from the horizontal at a velocity of 4 m/s. Air sent from air outlet 5 reaches the ceiling of room 20. Then, the air current flows along the ceiling owing to the Coanda effect without losing momentum and merges with another air current from the opposite air outlet 5. The merged air current flows downward and along the floor, is drawn from air inlet 4, and is discharged outside the room. Conditions under which the ions are generated are the same as those described above.

Figure 10:
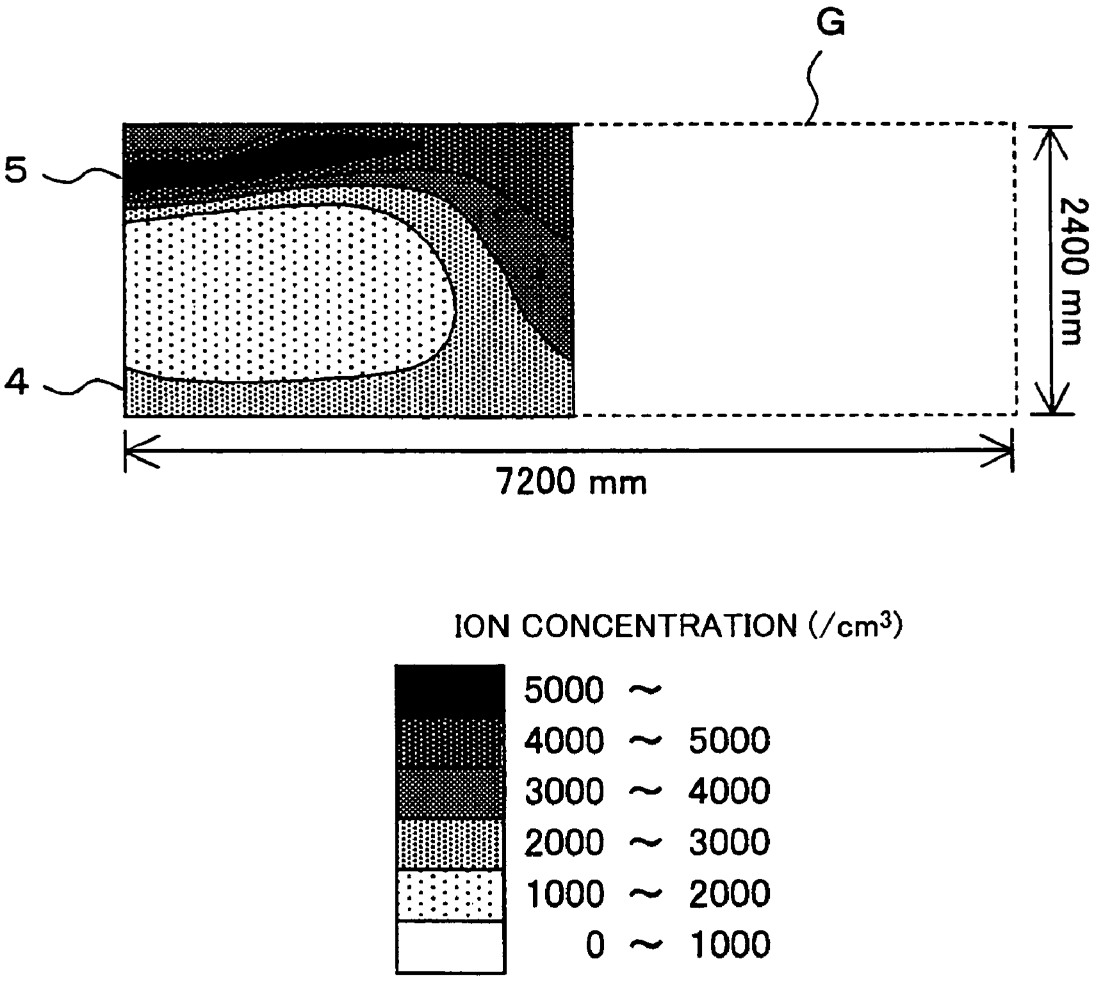
FIG. 10 is a graph illustrating another predicted result of the concentration distribution of microparticles.

FIG. 10 is a graph of another predicted result of the concentration distribution of microparticles. FIG. 10 illustrates only the left half of a predictive ion concentration distribution at a cross section G passing through the center of air outlets 5 and air inlets 4 illustrated in FIG. 9. Because the right half and the left half are symmetrical with respect to a line, FIG. 10 illustrates only the left half of the cross section G and omits the right half.

FIG. 10 shows that the ion concentration in the center of room 20 is higher than that in FIG. 8. However, a region having an ion concentration of 1000/$cm^3$ to 2000/$cm^3$ still spreads widely.

Figure 11:
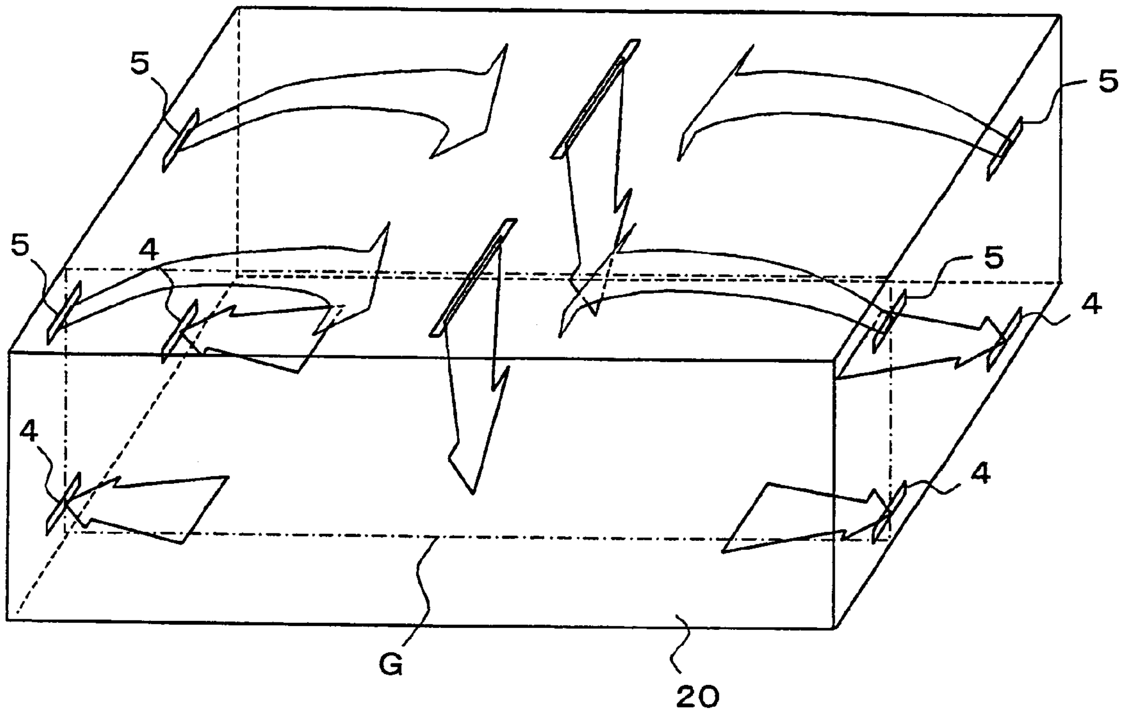
FIG. 11 is still another schematic view illustrating the behavior of air currents in a room.

To minimize a region having an ion concentration of less than 2000/$cm^3$, another model is intended to send air currents containing ions (conditions under which the ions are generated are the same as those described above) downward from the center of the ceiling at a velocity of 4 m/s. FIG. 11 is still another schematic view illustrating the behavior of air currents in the room. FIG. 11 illustrates the behavior of air currents in the room when the air currents are sent downward from the center of the ceiling at a velocity of 4 m/s, in addition to the air currents sent from air outlets 5 at an angle of 20 degrees upward from the horizontal at a velocity of 4 m/s.

Figure 12:
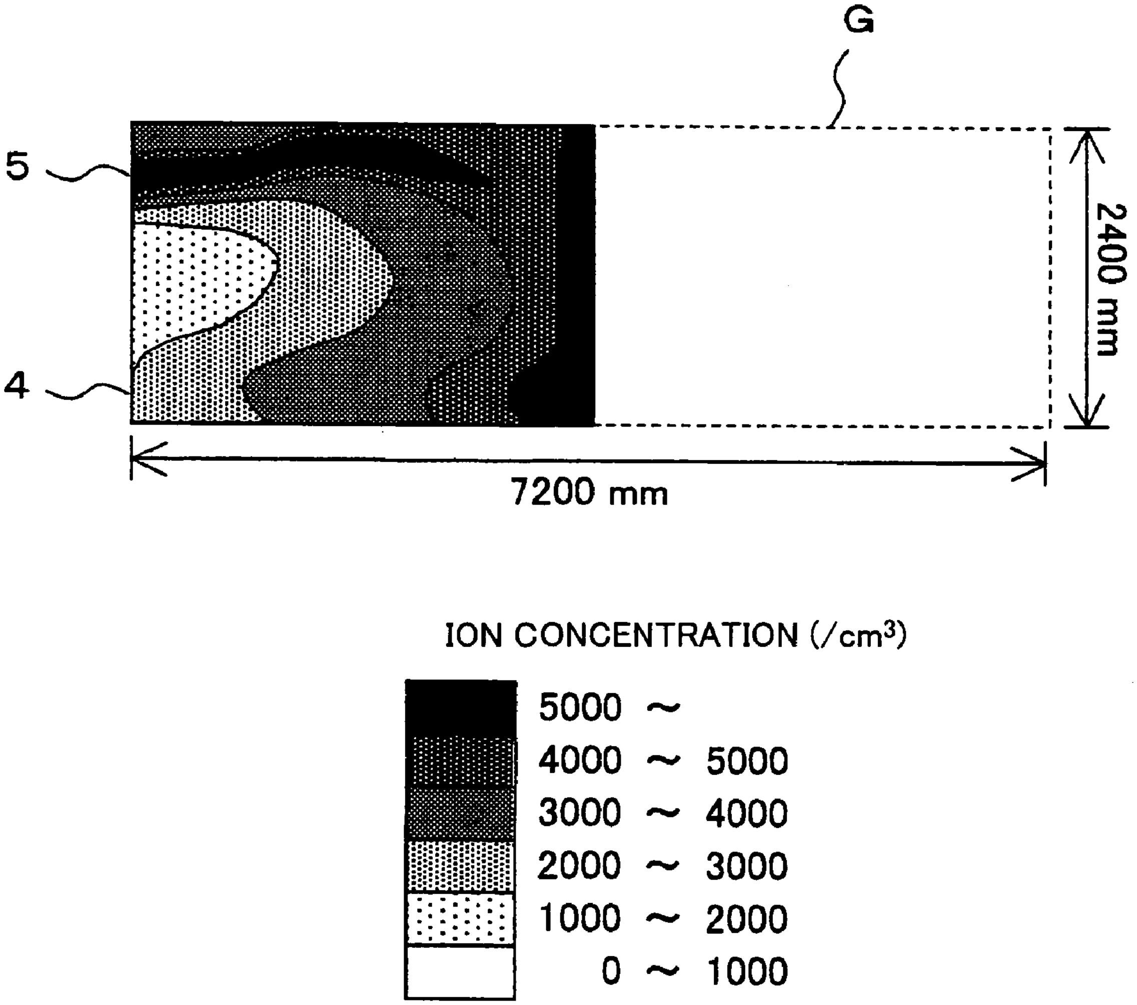
FIG. 12 is a graph illustrating still another predicted result of the concentration distribution of microparticles.

FIG. 12 is a graph of another predicted result of the concentration distribution of microparticles. FIG. 12 illustrates only the left half of a predictive ion concentration distribution at a cross section G passing through the center of air outlets 5 and air inlets 4 (see FIG. 10). FIG. 12 illustrates only the left half of the cross section G. Because the right half and the left half are symmetrical with respect to a line, the right half is omitted. FIG. 11 shows that a region having an ion concentration of less than 2000/$cm^3$ is much smaller than that in FIG. 10.

A method for controlling an air current that can effectively diffuse microparticles in a room can easily be achieved using an analyzer according to the present embodiment. Thus, by designing a room on the basis of the results, a room that can maximize the effects of microparticle diffusion can easily be designed. Furthermore, a building including the room can easily be designed without complicated processes such as an experiment. In other words, by determining parameters defining an analytical model in which the concentration of microparticles in a room satisfies a predetermined condition, a room defined by the parameters can be designed.

While the design parameters have been examined in terms of the blow direction and the locations and the number of the air outlets, the design parameters may also be examined in terms of the size and the shape of the room. Furthermore, the analyzer according to the third embodiment can be used to perform the procedure described above automatically by iterative calculations. Thus, the same effect as described above can be achieved more easily.

Since a building designed with analyzer 100 is designed with the diffusion of microparticles in mind, a building that exhibits very large effects of microparticle diffusion can easily be constructed without complicated processes such as an experiment.

Fifth Embodiment

A method for designing a room that achieves sufficient effects of microparticles with the analyzers according to the first to third embodiments will be described below. For example, a microparticle diffusing device is a large air conditioner, such as an air conditioner for a large building, an air conditioner for a whole building, or a multi air conditioner for business use, the arrangement and the number of microparticle diffusing devices are often restricted or limited in terms of workability. In this case, it is difficult to achieve the maximum effect of microparticles diffused by a microparticle diffusing device.

Figure 13:
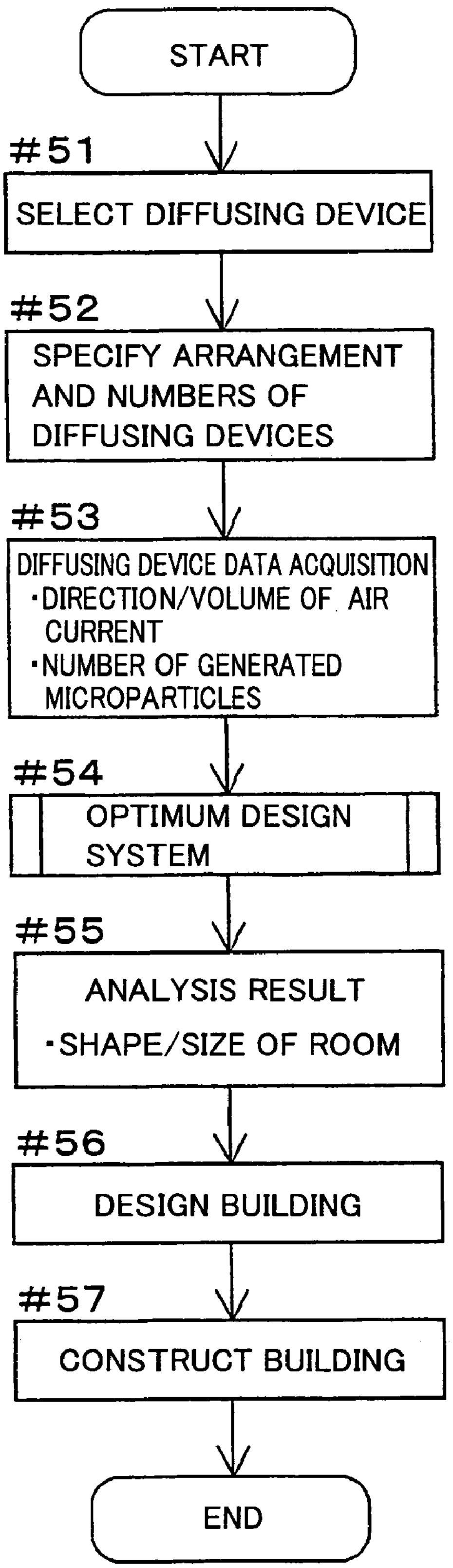
FIG. 13 is a flow chart illustrating a procedure for designing a room by a design method according to a fifth embodiment.

The present method determines the shape and the size of a room that can achieve the maximum effect of microparticles diffused by an existing microparticle diffusing device. FIG. 13 is a flow chart illustrating a procedure for designing a room by a design method according to a fifth embodiment. Specifically, a user of the analyzer initially selects a microparticle diffusing device in step #51. When the microparticle diffusing device is an air conditioner, the user must specify the refrigeration capacity, the type, the manufacturer, and the like.

In step #52, the user defines the arrangement and the number of microparticle diffusing devices. When the microparticle diffusing device is an air conditioner, the arrangement and the number of microparticle diffusing devices are often restricted or limited in terms of workability of piping and the like. The user must therefore define them.

In step #53, the analyzer acquires a master data of the microparticle diffusing device selected in step #51. For example, the analyzer acquires information, such as the direction and the volume of an air current and the number of generated microparticles, at a high power operation and a low power operation.

In step #54, the user inputs the arrangement and the number of microparticle diffusing devices, the direction and the volume of an air current, and the number of generated microparticles as fixed values to the system according to the third embodiment, and analyzes them. In this case, in FIG. 6, step #43 is always Yes and step #44 is always No, and in step #45, the arrangement and the number of the microparticle diffusing devices are not changed. The user changes only the shape/size of the room.

In step #55, the user obtains the shape and the size of the room as the results of the analysis performed in step #54. In step #56, the user designs a building on the basis of the shape and the size of the room obtained in step #55. In step #57, the user constructs the building.

Using the design method according to the fifth embodiment, a room that can maximize the effects of microparticle diffusion can easily be designed. Furthermore, a building including the room can easily be designed without complicated processes such as an experiment. Furthermore, a room that can sufficiently exploit the effects of microparticles by suitable diffusion of microparticles can easily be designed.

Sixth Embodiment

Figure 14:
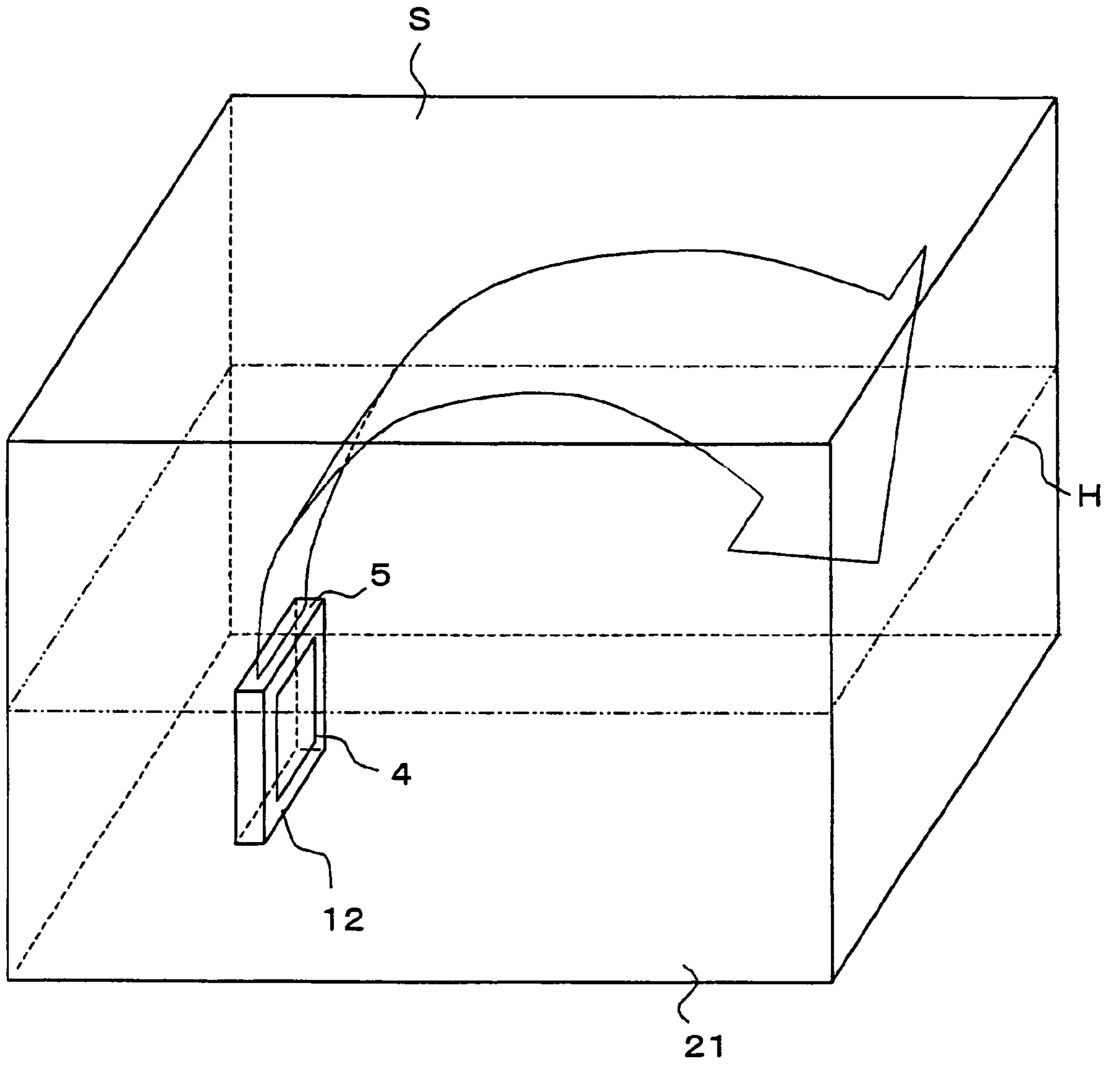
FIG. 14 is still another schematic view illustrating the behavior of air currents in a room.

A microparticle diffusing device designed by the analyzers according to the first to third embodiments will be described below. FIG. 14 is still another schematic view illustrating the behavior of air currents in room. In FIG. 14, air cleaner 12 is placed in room 21. Air cleaner 12 is a microparticle diffusing device. The main body has a generally rectangular parallelepiped shape having dimensions of 500 mm in height, 400 mm in width, and 200 mm in depth. Air cleaner 12 has air outlet 5 at the top surface and an air inlet 4 at the front surface. The air outlet has a rectangular parallelepiped shape of 250 mm×100 mm. The volume of blowing air is 6 $m^3$/min; that is, the blowing velocity is 4 m/s. Air cleaner 12 is placed on the floor 600 mm away from a side wall of room 21. The blow direction indicated by an arrow is 20 degrees on the left and 20 degrees frontward (70 degrees upward from the horizontal) facing the front of air cleaner 12 (the face on which the air inlet 4 is placed). The behavior of the air current sent at a blowing velocity of 4 m/s is indicated. Room 21 is 8 mats in size (2400 mm in height, 3600 mm in width, and 3600 mm in depth).

Figure 15:
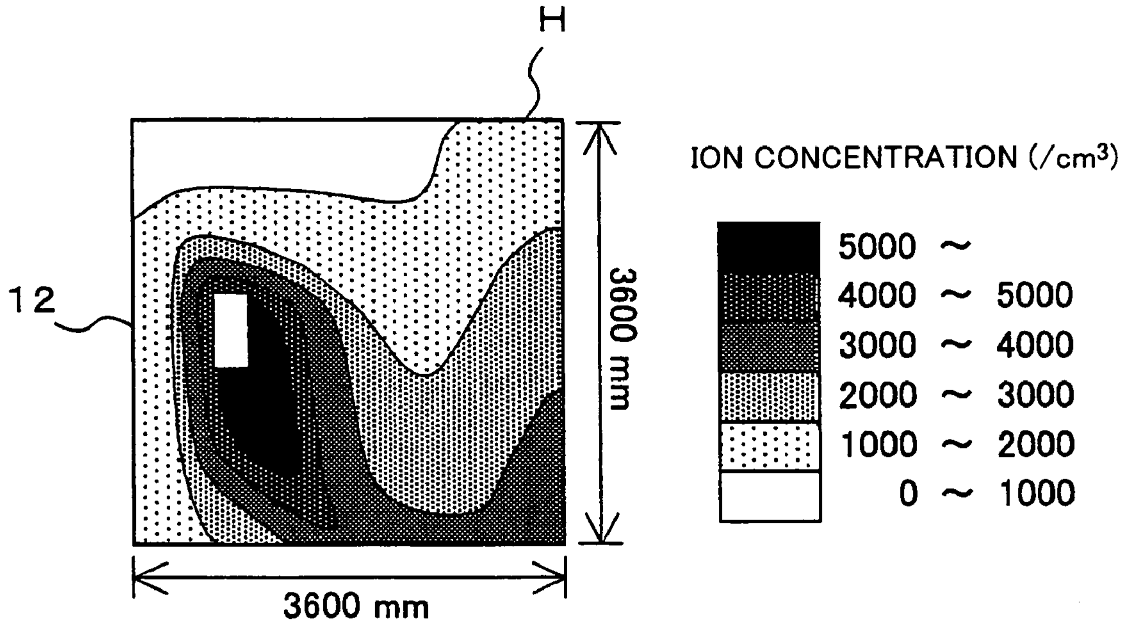
FIG. 15 is a graph illustrating still another predicted result of the concentration distribution of microparticles.

FIG. 15 is a graph of another predicted result of the concentration distribution of microparticles. FIG. 15 illustrates the concentration distribution of ions in room 21 predicted by the analyzer according to the first embodiment, when a mixture of equal numbers of positive ions $H^+(H_2O)_n$ and negative ions $O_2^-(H_2O)_m$ is sent on the air current from air outlet 5 of air cleaner 12. FIG. 15 illustrates a predictive ion concentration distribution in a plane at the half height of room 21, that is, the horizontal plane H at a height of 1200 mm (see FIG. 14). In this embodiment, for example, the concentrations of the two ion species in the vicinity of the position at which the ions are generated are also one million/$cm^3$ each. FIG. 15 shows that a region having an ion concentration of less than 2000/$cm^3$ spreads over the center of the room. Furthermore, a region having an ion concentration of less than 1000/$cm^3$ exists at a deep part of the room (upper center in FIG. 15). Hence, the ions do not spread over the entire room. As described above, academic research has already showed that at least 99% of airborne viruses die in two hours in a space containing at least 2000/$cm^3$ of $H^+(H_2O)_n$ and $O_2^-(H_2O)_m$ each. Hence, when air cleaner 12 is placed in room 21 illustrated in FIGS. 14 and 15 and ions are sent in the direction described above, the effect of killing airborne viruses is insufficient.

Thus, another model is intended to place air cleaner 12 in contact with a side wall of room 21 and send an air current in a direction of 20 degrees on the left and 0 degree frontward (90 degrees upward from the horizontal) facing the front of air cleaner 12 (the face on which the air inlet 4 is placed) at a velocity of 4 m/s.

Figure 16:
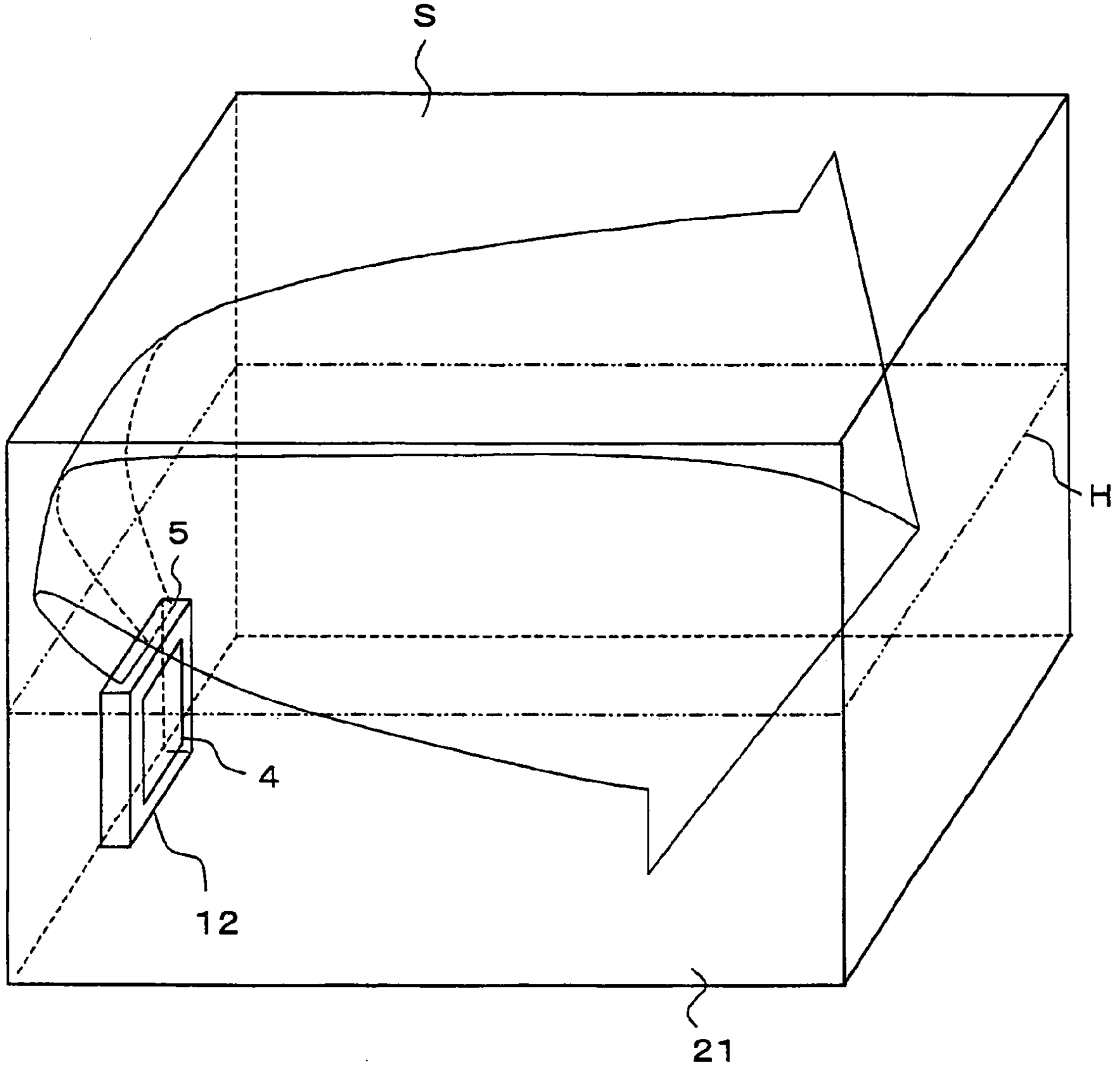
FIG. 16 is still another schematic view illustrating the behavior of air currents in a room.

FIG. 16 is still another schematic view illustrating the behavior of air currents in the room. FIG. 16 illustrates the behavior of air currents in room 21. Air cleaner 12 is placed in contact with a side wall of room 21. The blow direction is 20 degrees on the left and 0 degree frontward (90 degrees upward from the horizontal) facing the front of air cleaner 12 (the face on which air inlet 4 is placed). The blowing velocity of air currents is 4 n/s. Air sent from air outlet 5 flows to the top left corner of the room facing the front of air cleaner 12. The air flows along the ceiling and the left side wall of the room facing the front of air cleaner 12 owing to the Coanda effect without losing momentum. The air circulates widely through room 21. Conditions under which ions are generated are the same as those described above.

Figure 17:
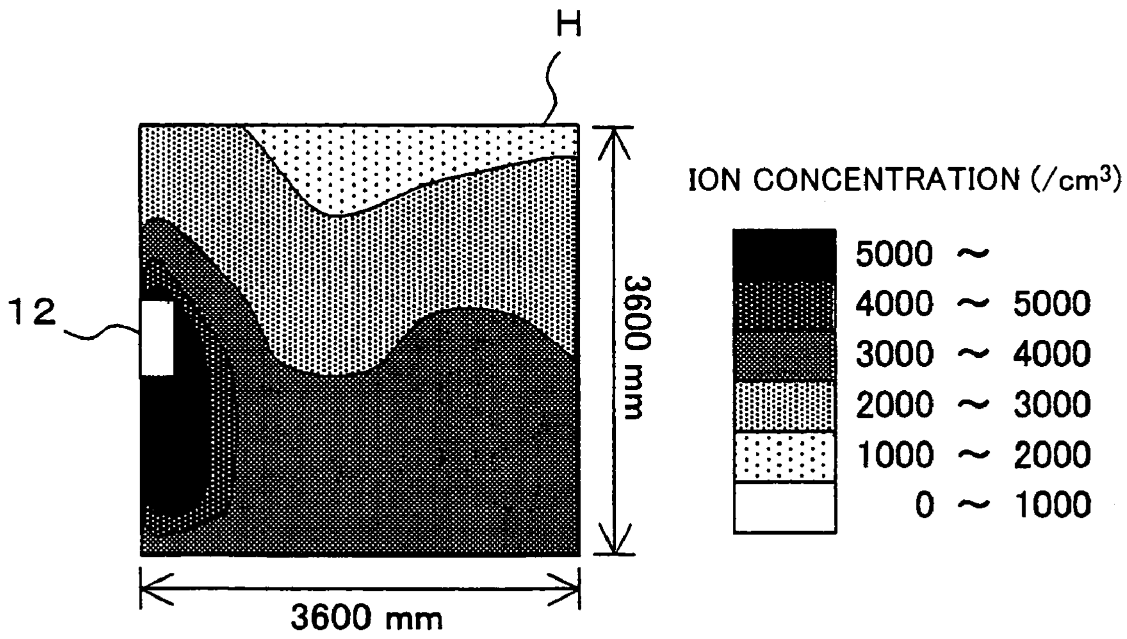
FIG. 17 is a graph illustrating still another predicted result of the concentration distribution of microparticles.

FIG. 17 is a graph of another predicted result of the concentration distribution of microparticles. FIG. 17 illustrates the concentration distribution of ions in room 21 predicted with the system according to the first embodiment. As shown in FIG. 15, FIG. 17 illustrates a predictive ion concentration distribution in a plane at the half height of room 21, that is, the horizontal plane H at a height of 1200 mm (see FIG. 16). FIG. 17 shows that the ion concentration at the center of the room is higher than that in the concentration distribution of microparticles illustrated in FIG. 15. Since the air current flows along the ceiling and the side wall owing to the Coanda effect without losing momentum, the ions flow farther before being attenuated. However, a region having an ion concentration of 1000/$cm^3$ to 2000/$cm^3$ still exists.

Figure 18:
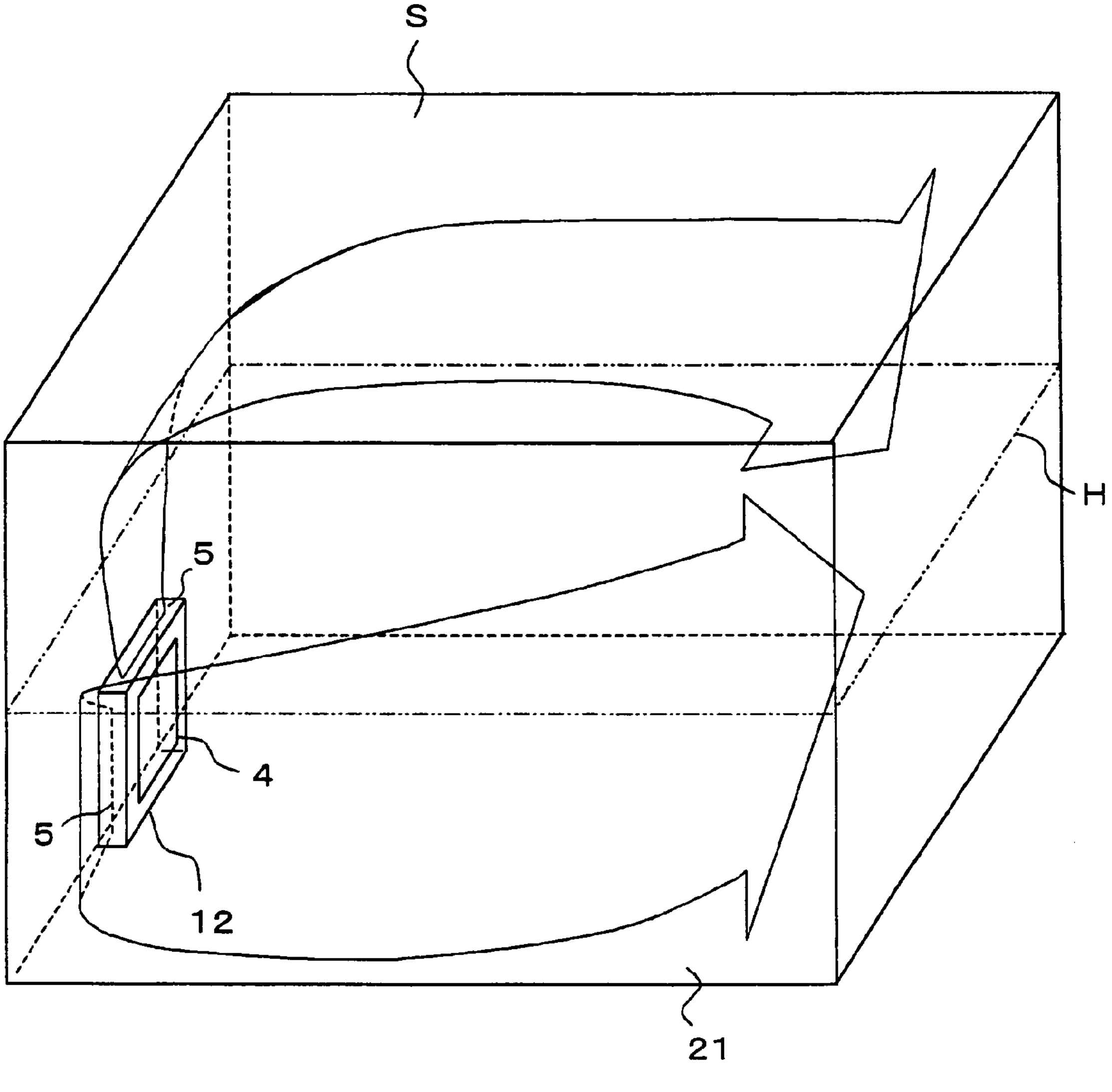
FIG. 18 is still another schematic view illustrating the behavior of air currents in a room.

Thus, another model is intended to minimize a region having an ion concentration of less than 2000/$cm^3$. FIG. 18 is still another schematic view illustrating the behavior of air currents in the room. As illustrated in FIG. 18, air cleaner 12 is placed in contact with a side wall of room 21. Air cleaner 12 has two rectangular parallelepiped air outlets 5 each having a size of 250 mm×40 mm in the top surface and in the left side as one faces the front of air cleaner 12. The volume of blowing air is 3 $m^3$/min each and 6 $m^3$/min (the same as described above) in total. That is, each blowing velocity is 5 m/s. The blow direction is straight upward from air outlet 5 in the top surface and horizontal from air outlet 5 in the left side of air cleaner 12.

In FIG. 18, the air sent from air outlets 5 flows straight upward and horizontally (to the left), facing the front of air cleaner 12. The air current flows along the ceiling and the left side wall of the room facing the front of air cleaner 12 owing to the Coanda effect without losing momentum. The air circulates widely through room 21. Conditions under which ions are generated are the same as those described above.

Figure 19:
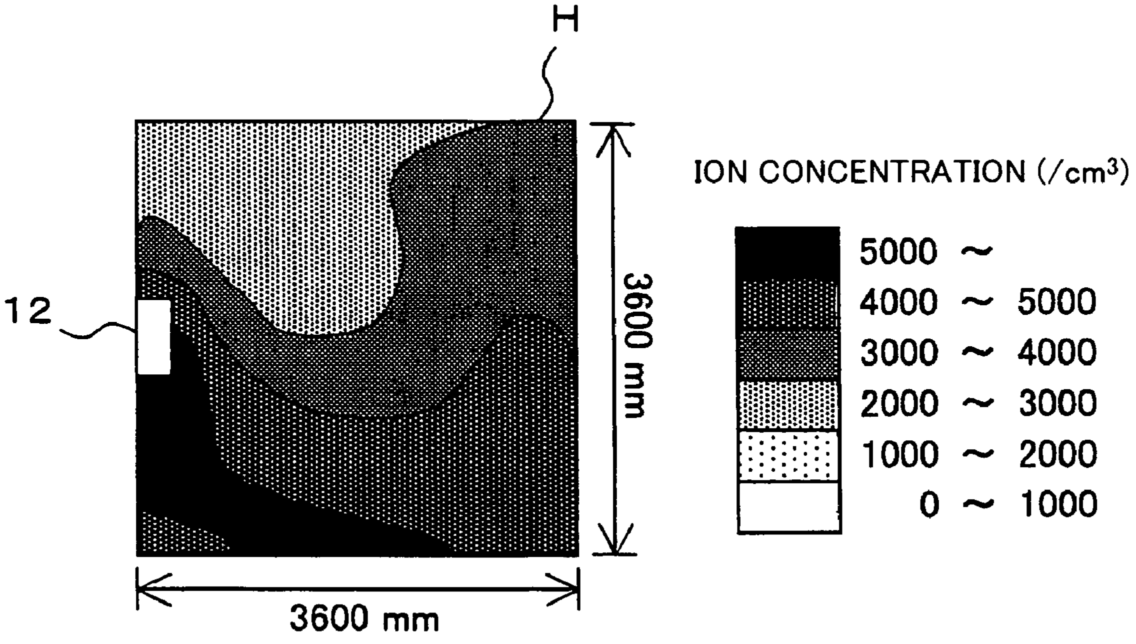
FIG. 19 is a graph illustrating still another predicted result of the concentration distribution of microparticles.

FIG. 19 is a graph of another predicted result of the concentration distribution of microparticles. FIG. 19 illustrates a result of the behavior of air currents in the room illustrated in FIG. 18 predicted with the analyzer according to the first embodiment. As in FIGS. 15 and 17, FIG. 19 illustrates a predictive ion concentration distribution in a plane at the half height of room 21, that is, the horizontal plane H at a height of 1200 mm (see FIG. 18). FIG. 19 shows that the ions flow wider and farther than that in the concentration distribution of microparticles illustrated in FIG. 17. In addition, there is no region having an ion concentration of less than 1000/$cm^3$. Hence, the effect of killing airborne viruses is sufficient.

Using the design method according to the sixth embodiment, the location of a microparticle diffusing device and the shape of an air outlet that can effectively diffuse microparticles in an existing room can easily be determined in a design stage. Thus, by designing a microparticle diffusing device on the basis of the results, the designed microparticle diffusing device has a structure that can optimize the diffusion of microparticles in a room to which the microparticle diffusing device is to be installed. Thus, a microparticle diffusing device having the largest effects of microparticle diffusion can be obtained without complicated processes such as an experiment. In other words, by determining a boundary condition under which the concentration of microparticles in a room satisfies a predetermined condition, a microparticle diffusing device defined by the boundary condition can be designed.

While the design parameters have been examined in terms of the location of a microparticle diffusing device, the blow direction, the shape of the air outlets, and the locations and the number of the air outlets, the design parameters may be examined in terms of the volume of air, the number of generated microparticles, and other design parameters. Furthermore, the system according to the third embodiment can be used to perform the procedure described above automatically by iterative calculations. Thus, the same effect as described above can be achieved more easily.

The microparticle diffusing device designed with analyzer 100 has a structure that can optimize in a design stage the diffusion of microparticles in a room in which the device is to be installed. Hence, a microparticle diffusing device having the largest effects of microparticle diffusion can be designed without complicated processes such as an experiment.

Seventh Embodiment

Next, a method for designing a microparticle diffusing device that can sufficiently achieve the effects of microparticles will be described below. Examples of a microparticle diffusing device installed in a room include an air conditioner, a humidifier, an air cleaner, and other various devices. The location of a microparticle diffusing device in a room affects the diffusibility of microparticles, such as negative ions, water vapor, tiny drops of water, or a fragrant component, in the room. In particular, when diffused microparticles have limited lives, the diffusibility of microparticles in a room is extremely affected. Hence, to improve the diffusibility of microparticles of a microparticle diffusing device, the microparticle diffusing device must be designed by considering the installation location of the microparticle diffusing device, the blow direction and the blowing velocity of microparticles, the volume of blowing air, the shape of an air outlet, and a flow pass from the position at which the microparticles are generated to the air outlet, relative to the size and the shape of a room in which the device is to be installed.

A design method according to the present embodiment determines the suitable installation location of a microparticle diffusing device, the blow direction of microparticles, the volume and the velocity of blowing air, and the shape of an air outlet to diffuse microparticles in a room so that the maximum effects of microparticle diffusion can be achieved.

Figure 20:
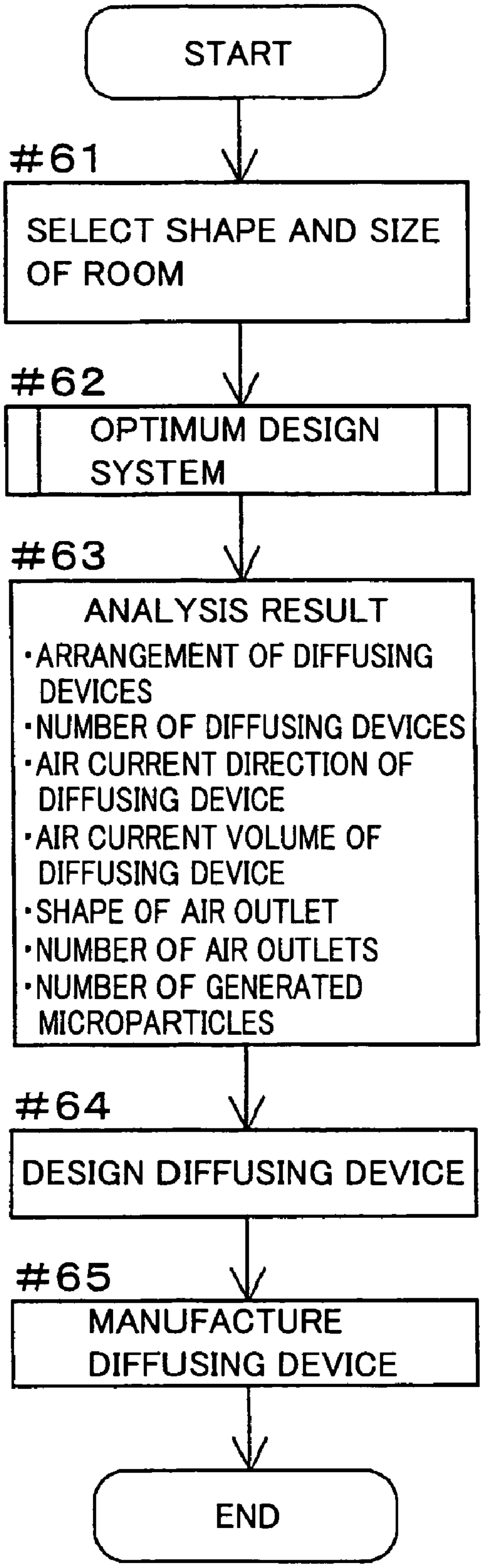
FIG. 20 is a flow chart illustrating a procedure of a method for designing a microparticle diffusing device according to a seventh embodiment.

FIG. 20 is a flow chart illustrating a procedure of a method for designing a microparticle diffusing device according to a seventh embodiment. Specifically, an architect of a microparticle diffusing device initially defines the shape and the size of a room in which the microparticle diffusing device is to be installed in step #61. When the microparticle diffusing device is an air cleaner, the number of mats in the room and the time required for air cleaning, that is, the number of mats to which the air cleaning capacity can be applied is indicated as a criterion. Furthermore, even when the number of mats is the same, various shapes of the room, such as square and rectangular, may be contemplated.

In step #62, the architect inputs the shape and the size of the room as fixed values to the system according to the third embodiment. The system analyzes the concentration distribution. In this case, in FIG. 6, steps #43 and #44 are always Yes, and in step #45, the shape/size of the room and the number of microparticle diffusing devices are not changed, and only the location of a microparticle diffusing device is changed.

In step #63, the architect obtains the arrangement and the number of microparticle diffusing devices, the direction and the volume of air in the microparticle diffusing devices, the shape and the number of air outlets, and the number of generated microparticles as the results of the analysis performed in step #62.

In step #64, the architect designs a microparticle diffusing device based on the arrangement and the number of microparticle diffusing devices, the direction and the volume of air in the microparticle diffusing devices, the shape and the number of air outlets, and the number of generated microparticles obtained in step #63. In step #65, the architect manufactures the microparticle diffusing device.

Using the design method according to the present embodiment, a microparticle diffusing device that can suitably diffuse microparticles in a room and maximize the effects of the microparticles can easily be obtained without complicated processes such as an experiment.

Eighth Embodiment

Next, a method for placing or installing a microparticle diffusing device in a room will be described below. This method determines a suitable arrangement and the number of microparticle diffusing devices that diffuse microparticles in an existing room so that the maximum effects of microparticle diffusion can be achieved.

In the following case, another microparticle diffusing device 10 is installed in room 21 in which indoor unit 1 of an air conditioner is installed, as illustrated in FIGS. 2, 3A, and 3B, to further increase the effects (disinfection effects) of microparticle positive ions $H^+(H_2O)_n$ and negative ions $O_2^-(H_2O)_m$.

In the states illustrated in FIGS. 2, 3A, and 3B, a region having an ion concentration of $1000/cm^3$ to $2000/cm^3$ accounts for most of room 21. Thus, as microparticle diffusing device 10, circulator 11 is installed on a lower part of a side wall opposite to a side wall on which indoor unit 1 of an air conditioner is installed.

Figure 21:
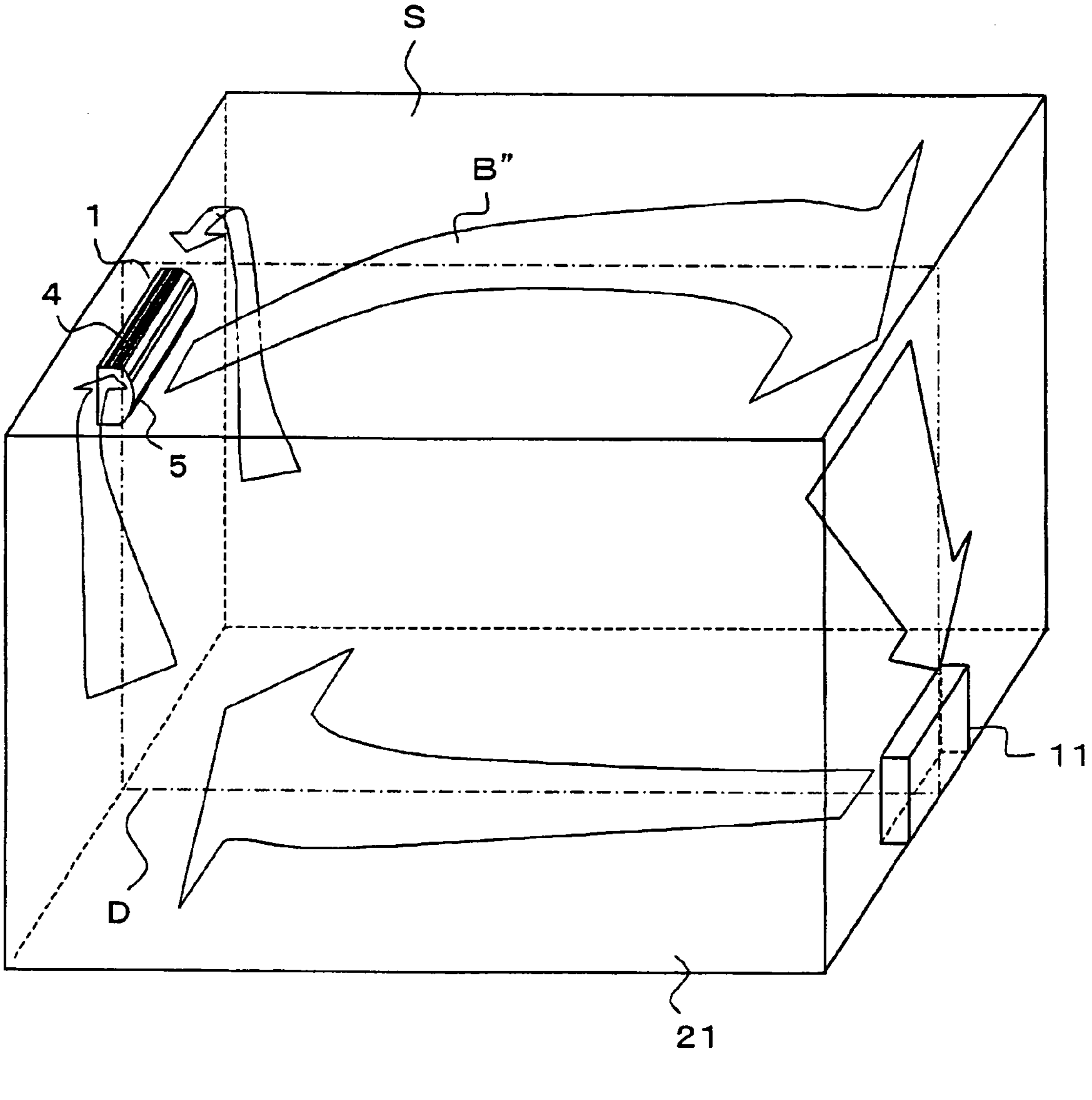
FIG. 21 is still another schematic view illustrating the behavior of air currents in a room.
Figure 22:
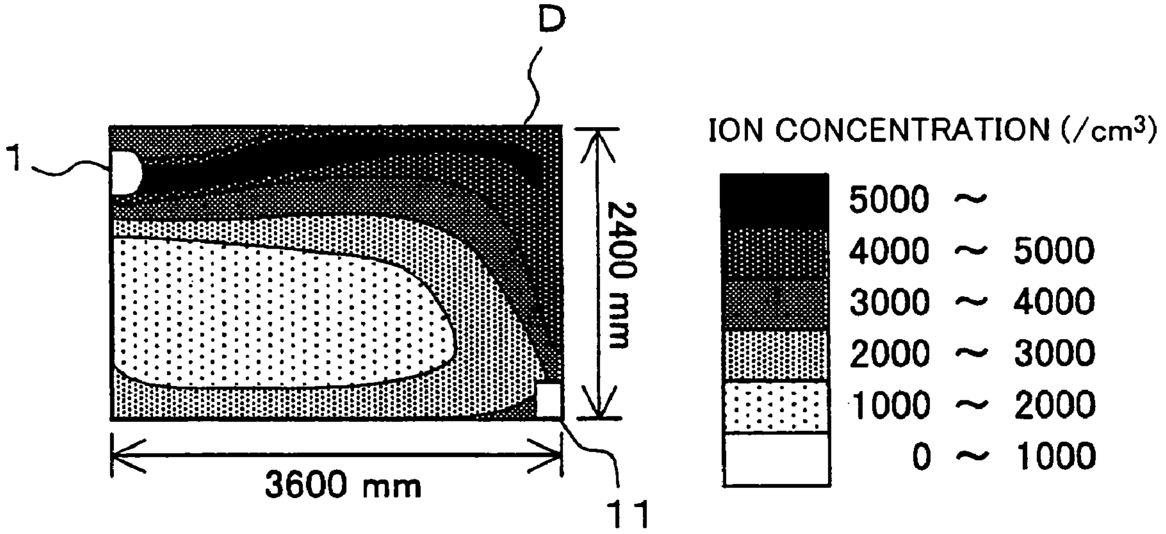
FIG. 22 is a graph illustrating still another predicted result of the distribution of microparticles.

FIG. 21 is still another schematic view illustrating the behavior of air currents in the room. In addition to the state illustrated in FIG. 2, FIG. 21 illustrates the behavior of air currents in the room when circulator 11 is installed on a lower part of a side wall opposite to a side wall on which indoor unit 1 of an air conditioner is installed. FIG. 22 is a graph of another predicted result of the distribution of microparticles. FIG. 22 illustrates a result of the ion concentration distribution at a central cross section of room 21 indicated by an alternate long and short dashed line D in FIG. 21, predicted with the system according to the first embodiment. FIG. 22 shows that circulator 11 improves the ion concentration distribution. However, a region having an ion concentration of less than $2000/cm^3$ still widely spreads over a living space in room 21.

Figure 23:
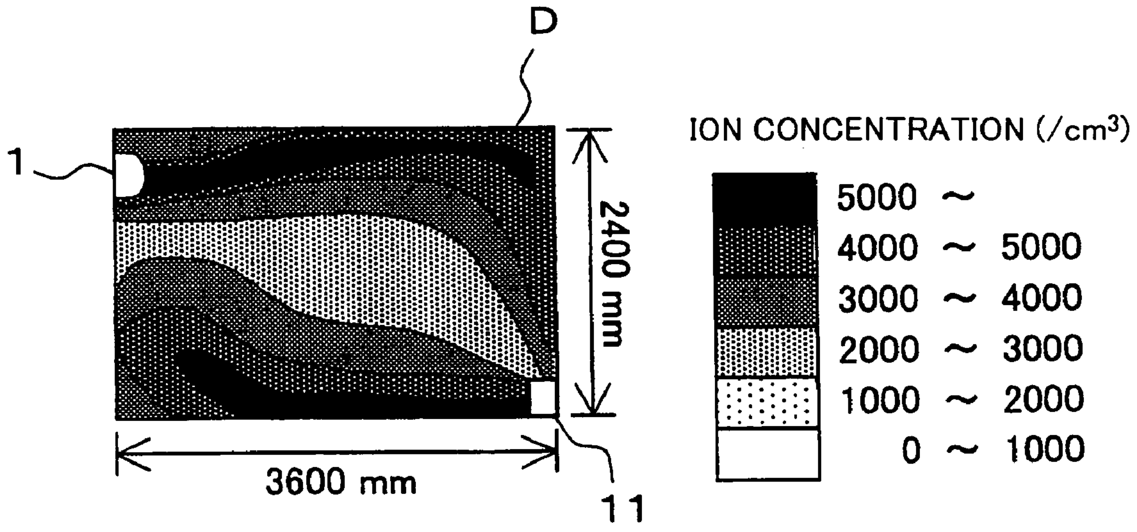
FIG. 23 is a graph illustrating still another predicted result of the distribution of microparticles.

FIG. 23 is a graph of another predicted result of the distribution of microparticles. FIG. 23 illustrates the concentration distribution of ions at a central cross section of room 21, predicted with the system according to the first embodiment. Circulator 11 is provided with an ion generator. While the behavior of an air current is unchanged, a mixture of equal numbers of positive ions $H^+(H_2O)_n$ and negative ions $O_2^-(H_2O)_m$ is sent from the air outlet.

Furthermore, the ion generator is adjusted so that the concentrations of the two ion species are one million/$cm^3$ each in the vicinity of the position at which the ions are generated in circulator 11. Comparison of FIG. 22 and FIG. 23 shows that the addition of the ion generator to circulator 11 greatly improves the ion concentration distribution and eliminates the region having an ion concentration of less than $2000/cm^3$ at the central cross section of room 21.

As described above, the analyzer according to the first embodiment can be used to estimate the location of a microparticle diffusing device in a room, the blow direction of microparticles, and the number of the microparticle diffusing devices, thus determining an installation plan. According to this method, a suitable arrangement and the number of microparticle diffusing devices can be determined with the system when the microparticle diffusing devices are placed or installed in a room. Thus, the arrangement and the number of microparticle diffusing devices that can suitably diffuse microparticles in the room can easily be obtained without complicated processes such as an experiment. This can reduce the time required to place or install the microparticle diffusing devices and greatly reduce the cost.

Furthermore, the system according to the third embodiment can be used to perform the procedure described above automatically by iterative calculations. Thus, the same effect as described above can be achieved more easily.

Furthermore, in the method for placing or installing microparticle diffusing devices according to the present invention, when a user of the microparticle diffusing devices places or installs the microparticle diffusing devices in a room, the user can previously know a suitable arrangement and the number of the microparticle diffusing devices with the analysis system. Thus, the arrangement and the number of the microparticle diffusing devices that can suitably diffuse microparticles in the room can easily be obtained without complicated processes such as an experiment. This can reduce the time required to place or install the microparticle diffusing devices and greatly reduce the cost.

Ninth Embodiment

The analyzer according to the first to eighth embodiments can be realized with a computer. FIG. 24 is a schematic block diagram illustrating a hardware configuration of a computer. In FIG. 24, computer 100A includes central processing unit (CPU) 111, read only memory (ROM) 112 storing a program sent to an operating system, random access memory (RAM) 113 for storing a program to be executed and data during program execution, hard disk 114, mouse 117, keyboard 118, display 119, printer 120, and compact disc read only memory (CD-ROM) drive 115, each connected to bus 116. CD-ROM 112 is inserted into CD-ROM drive 115. Since the operation of a computer having such a configuration is well known, its details will not be repeated here.

In computer 100A, CPU 111 executes an analysis program to realize the analyzers according to the first to eighth embodiments. This program may be provided as a program product stored in a recording medium, as described below.

Specifically, in general, such a program is distributed in a recording medium such as CD-ROM 112, is read from the recording medium with CD-ROM drive 115, and temporarily stored in hard disk 114. The program is read out to RAM 113 from hard disk 114 and is executed by CPU 111.

The recording medium is not limited to CD-ROM 112 and hard disk 114, and may be a medium that nonvolatilely stores a program, for example, a flexible disk, a cassette tape, an optical disk (a magnetic optical disc (MO)/a mini disc (MD)/a digital versatile disc (DVD), an integrated circuit (IC) card (including a memory card), an optical card, a semiconductor memory, such as a mask ROM, an erasable programmable ROM (EPROM), an electrically erasable and programmable ROM (EEPROM), or a flash ROM.

The term "program" used herein refers to not only a program that can directly be executed by CPU 111, but also a program of a source program type, a compactly displayed program, and an encrypted program.

It is to be understood that the embodiments disclosed herein are illustrated by way of example and not by way of limitation in all respects. The scope of the present invention is defined by the appended claims rather than by the description described above. All changes that fall within the scope of the claims and the equivalence thereof are therefore intended to be embraced by the claims.

The invention claimed is:

1. A method for predicting the concentration distribution of microparticles, comprising the steps of:

determining a flow field in a room; determining an age-of-air distribution with a location of microparticles immediately after their generation delivered to the room or the location at which the microparticles are discharged into the room as a starting point, on the basis of the flow field in the room; and using conversion unit for converting the age of air with said location as the starting point into a concentration of microparticles;

wherein said converting step converts said age of air into said concentration of microparticles using a predetermined relation defining a relationship between an elapsed time t and a concentration X of microparticles, based on a type of said microparticles and a generated amount of microparticles.

2. The method for predicting the concentration distribution of microparticles according to claim 1, wherein said relation is expressed by the following equation (1):

$$X(t)=\alpha/(t-\beta)+\gamma,\ X(t)\geqq\delta \qquad (1)$$

based on constants α, β, γ, and δ, wherein said constants α, γ, and δ, depend on the type of ions or diffused microparticles, and are determined in an experiment, and said constant β is defined by the starting point of the elapsed time.

3. The method for predicting the concentration distribution of microparticles according to claim 1, further comprising the steps of:

constructing an analytical model in which a room is divided into microelements; and setting a boundary condition to simulate said flow field, wherein said step of determining the flow field in a room determines the flow field in the room on the basis of said boundary condition and parameters defining said analytical model, said method further comprising the steps of changing said boundary condition to determine a boundary condition corresponding to a concentration of microparticles that satisfies a predetermined condition among the converted concentration of microparticles.

4. The method for predicting the concentration distribution of microparticles according to claim 3, wherein said boundary condition includes a direction and velocity of an air current.

5. The method for predicting the concentration distribution of microparticles according to claim 1, further comprising the steps of:

constructing an analytical model in which a room is divided into microelements;

setting a boundary condition to simulate said flow field; and changing parameters defining said analytical model to determine parameters corresponding to a concentration of microparticles that satisfies a predetermined condition among the converted concentration of microparticles.

6. The method for predicting the concentration distribution of microparticles according to claim 5, wherein said parameters include a size of the room, a shape of the room, and the concentration of microparticles at the starting point.

7. The method for predicting the concentration distribution of microparticles according to claim 1, further comprising the step of changing the concentration of microparticles at the starting point of the elapsed time to determine the concentration of microparticles at said starting point corresponding to a concentration of microparticles that satisfies a predetermined condition among the converted concentration of microparticles.

8. An analyzer for performing the method for predicting the concentration distribution of microparticles according to claim 1.

9. A computer-readable media for storing a program for predicting the concentration distribution of microparticles for causing a computer to execute the method for predicting the concentration distribution of microparticles according to claim 1.

10. A building comprising:

a sidewall;

a floor;

a ceiling; and a room encompassed by a space surrounded by said sidewall, said floor, and said ceiling, wherein the distance between said floor and said ceiling, the arrangement and layout of said sidewall, and the shape and size of said space are determined by parameters defining an analytical model in which a room is divided into microelements, when the concentration distribution of microparticles determined by the method for predicting the concentration distribution of microparticles according to claim 1 satisfies a predetermined condition.

11. A microparticle diffusing device having a boundary condition for simulating a flow field and a concentration at a starting point when the concentration distribution of microparticles satisfies a predetermined condition, comprising:

a microparticle generator generating microparticles from a microparticle generation site;

an air blow path conveying microparticles generated from said microparticle generator; and an air outlet formed at an end of said air blow path to discharge microparticles;

wherein the size, shape, blowing direction, blowing velocity, and blowing volume of said air outlet, and the generated amount of microparticles are determined using the method for predicting the concentration distribution of microparticles according to claim 1.

12. A method for predicting the concentration distribution of microparticles, comprising the steps of:

determining a flow field in a room; determining an age-of-air distribution with a location of microparticles immediately after their generation delivered to the room or the location at which the microparticles are discharged into the room as a starting point, on the basis of the flow field in the room; and using conversion unit for converting the age of air with said position as the starting point into a concentration X of microparticles;

wherein said converting step converts said age of air into said concentration of microparticles using a predetermined relation defining a relationship between an elapsed time t and an attenuation rate of microparticles, based on a type of said microparticles and a generated amount of microparticles.

13. The method for predicting the concentration distribution of microparticles according to claim 12, wherein said relation is expressed by the following equation (2):

$$dX/dt=-\alpha_1X^2,\ X(0)=1/\beta_1 \qquad (2)$$

based on constants $\alpha_1$ and $\beta_1$, and wherein said constant $\alpha_1$ depends on the type of ions or diffused microparticles, and is determined in an experiment, and said constant $\beta_1$ is defined by the generated amount of microparticles.

14. The method for predicting the concentration distribution of microparticles according to claim 12, further comprising the steps of:

constructing an analytical model in which a room is divided into microelements; and setting a boundary condition to simulate said flow field;

wherein said step of determining the flow field in a room determines the flow field in the room on the basis of said boundary condition and parameters defining said analytical model, said method further comprising the steps of changing said boundary condition to determine a boundary condition corresponding to a concentration of microparticles that satisfies a predetermined condition among the converted concentration of microparticles.

15. The method for predicting the concentration distribution of microparticles according to claim 14, wherein said boundary condition includes a direction and velocity of an air current.

16. The method for predicting the concentration distribution of microparticles according to claim 12, further comprising the steps of:

constructing an analytical model in which a room is divided into microelements;

setting a boundary condition to simulate said flow field; and changing parameters defining said analytical model to determine parameters corresponding to a concentration of microparticles that satisfies a predetermined condition among the converted concentration of microparticles.

17. The method for predicting the concentration distribution of microparticles according to claim 16, wherein said parameters include a size of the room, a shape of the room, and the concentration of microparticles at the starting point.

18. An analyzer for performing the method for predicting the concentration distribution of microparticles according to claim 12.

19. A computer-readable media for storing a program for predicting the concentration distribution of microparticles for causing a computer to execute the method for predicting the concentration distribution of microparticles according to claim 12.

20. A method for arranging or installing a microparticle diffusing device in a room, comprising the step of designing an appropriate position of arrangement and number of arrangement of microparticle diffusing devices by the program product according to claim 19.

21. A building comprising:

a sidewall;

a floor;

a ceiling; and a room encompassed by a space surrounded by said sidewall, said floor, and said ceiling, wherein the distance between said floor and said ceiling, the arrangement and layout of said sidewall, and the shape and size of said space are determined by parameters defining an analytical model in which a room is divided into microelements, when the concentration distribution of microparticles determined by the method for predicting the concentration distribution of microparticles according to claim 12 satisfies a predetermined condition.

22. A microparticle diffusing device having a boundary condition for simulating a flow field and a concentration at a starting point when the concentration distribution of microparticles satisfies a predetermined condition, comprising:

a microparticle generator generating microparticles from a microparticle generation site;

an air blow path conveying microparticles generated from said microparticle generator; and an air outlet formed at an end of said air blow path to discharge microparticles;

wherein the size, shape, blowing direction, blowing velocity, and blowing volume of said air outlet, and the generated amount of microparticles are determined using the method for predicting the concentration distribution of microparticles according to claim 12.

* * * * *